(12) United States Patent
Hahnfeldt et al.

(10) Patent No.: US 7,638,273 B2
(45) Date of Patent: Dec. 29, 2009

(54) GENERATION AND USE OF VASCULOGENIC TUMORS AND PRODUCTS DERIVED FROM SAME

(75) Inventors: Philip Hahnfeldt, Wellesley, MA (US); Lynn Hlatky, Wellesley, MA (US)

(73) Assignee: Caritas St. Elizabeth's Medical Center of Boston, Inc., Boston, MA (US)

( * ) Notice: Subject to any disclaimer, the term of this patent is extended or adjusted under 35 U.S.C. 154(b) by 291 days.

(21) Appl. No.: 11/582,872

(22) Filed: Oct. 18, 2006

(65) Prior Publication Data

US 2007/0098637 A1    May 3, 2007

Related U.S. Application Data

(60) Provisional application No. 60/728,033, filed on Oct. 18, 2005.

(51) Int. Cl.
*C12Q 1/00* (2006.01)
*G01N 33/50* (2006.01)

(52) U.S. Cl. .............................. 435/4; 436/63
(58) Field of Classification Search ................ None
See application file for complete search history.

(56) References Cited

FOREIGN PATENT DOCUMENTS

| WO | WO9749827 | * | 12/1997 |
| WO | WO 01/00859 A1 | | 1/2001 |
| WO | WO 2004/006831 A2 | | 1/2004 |

OTHER PUBLICATIONS

Duda et al (Cancer Research, Sep. 1, 2004, vol. 64, pp. 5920-5924).*
Hatzopoulos et al (Development, 1998, vol. 125, pp. 1457-1468).*
Benedetti et al (Nature Medicine, 2000, vol. 6, pp. 447-450).*
Abstract of Siddiqui et al (Oncology Reports, 2005, vol. 14, pp. 1593-1597).*
Nobin et al (Brain Research Bulletin, 1982, vol. 781-797).*
Barcellos-Hoff MH et al., Extracellular signaling through the microenvironment: a hypothesis relating carcinogenesis, bystander effects, and genomic instability. Radiat Res. Nov. 2001;156(5 Pt 2):618-27.
Chamberlain LJ et al., Connective tissue response to tubular implants for peripheral nerve regeneration: the role of myofibroblasts. J Comp Neurol. Feb. 21, 2000;417(4):415-30.
Chiang C et al., Cyclopia and defective axial patterning in mice lacking Sonic hedgehog gene function. Nature. Oct. 3, 1996;383(6599):407-13.
Evans GR, Challenges to nerve regeneration. Semin Surg Oncol. Oct.-Nov. 2000;19(3):312-8.
Folkman J et al., Cancer: looking outside the genome. Nat Rev Mol Cell Biol. Oct. 2000;1(1):76-9.
Folkman J et al., Chapter 19: The logic of anti-angiogenic gene therapy. In: The Development of Human Gene Therapy. Cold Spring Harbor Laboratory Press, New York. 1999: 527-43.
Frank-Kamenetsky M et al., Small-molecule modulators of Hedgehog signaling: identification and characterization of Smoothened agonists and antagonists. J Biol. Nov. 6, 2002;1(2):10.
Fu SY et al., The cellular and molecular basis of peripheral nerve regeneration. Mol Neurobiol. Feb.-Apr. 1997;14(1-2):67-116.
Fuchs E et al., Socializing with the neighbors: stem cells and their niche. Cell. Mar. 19, 2004;116(6):769-78.
Fujimoto E et al., Basic fibroblast growth factor promotes extension of regenerating axons of peripheral nerve. In vivo experiments using a Schwann cell basal lamina tube model. J Neurocytol. Aug. 1997;26(8):511-28.
Hanahan D et al., The hallmarks of cancer. Cell. Jan. 7, 2000;100(1):57-70.
Hlatky L et al., Mammary fibroblasts may influence breast tumor angiogenesis via hypoxia-induced vascular endothelial growth factor up-regulation and protein expression. Cancer Res. Dec. 1, 1994;54(23):6083-6.
Hobson B et al., Endothelial proliferation in tumours and normal tissues: continuous labelling studies. Br J Cancer. Apr. 1984;49(4):405-13.
Ingham PW et al., Hedgehog signaling in animal development: paradigms and principles. Genes Dev. Dec. 1, 2001;15(23):3059-87.
Kee N et al., The utility of Ki-67 and BrdU as proliferative markers of adult neurogenesis. J Neurosci Methods. Mar. 30, 2002;115(1):97-105.
Kinzler KW et al., Lessons from hereditary colorectal cancer. Cell. Oct. 18, 1996;87(2):159-70.
Lai K et al., Sonic hedgehog regulates adult neural progenitor proliferation in vitro and in vivo. Nat Neurosci. Jan. 2003;6(1):21-7.
Lum L et al., The Hedgehog response network: sensors, switches, and routers. Science. Jun. 18, 2004;304(5678):1755-9.
Marti E et al., Requirement of 19K form of Sonic hedgehog for induction of distinct ventral cell types in CNS explants. Nature. May 25, 1995;375(6529):322-5.
Mukouyama YS et al., Sensory nerves determine the pattern of arterial differentiation and blood vessel branching in the skin. Cell. Jun. 14, 2002;109(6):693-705.
Nomi M et al., Principals of neovascularization for tissue engineering. Mol Aspects Med. Dec. 2002;23(6):463-83.
Pasca Di Magliano M et al., Hedgehog signalling in cancer formation and maintenance. Nat Rev Cancer. Dec. 2003;3(12):903-11.
Pola R et al., The morphogen Sonic hedgehog is an indirect angiogenic agent upregulating two families of angiogenic growth factors. Nat Med. Jun. 2001;7(6):706-11.
Ruiz I Altaba A et al., Gli and hedgehog in cancer: tumours, embryos and stem cells. Nat Rev Cancer. May 2002;2(5):361-72.
Shima DT et al., Vascular developmental biology: getting nervous. Curr Opin Genet Dev. Oct. 2000;10(5):536-42.
Soker S et al., Neuropilin-1 is expressed by endothelial and tumor cells as an isoform-specific receptor for vascular endothelial growth factor. Cell. Mar. 20, 1998;92(6):735-45.

(Continued)

*Primary Examiner*—Karen A Canella
(74) *Attorney, Agent, or Firm*—Wolf, Greenfield & Sacks, P.C.

(57) ABSTRACT

Tumors can be directed into a vasculogenic program and used to regenerate tissues in a verterbrate host, identify factors originating from the tumor that are useful for tissue regeneration, and to generate such factors for use in a subject apart from the tumor itself.

6 Claims, 16 Drawing Sheets

OTHER PUBLICATIONS

Sondell M et al., Vascular endothelial growth factor is a neurotrophic factor which stimulates axonal outgrowth through the flk-1 receptor. Eur J Neurosci. Dec. 2000;12(12):4243-54.

Thayer SP et al., Hedgehog is an early and late mediator of pancreatic cancer tumorigenesis. Nature. Oct. 23, 2003;425(6960):851-6.

Watkins DN et al., Hedgehog signalling within airway epithelial progenitors and in small-cell lung cancer. Nature. Mar. 20, 2003;422(6929):313-7.

Williams JA et al., Identification of a small molecule inhibitor of the hedgehog signaling pathway: effects on basal cell carcinoma-like lesions. Proc Natl Acad Sci U S A. Apr. 15, 2003;100(8):4616-21.

Achilles et al., Heterogeneity of angiogenic activity in a human liposarcoma: a proposed mechanism for "no take" of human tumors in mice. J Natl Cancer Inst. Jul. 18, 2001;93(14):1075-81.

Gimble et al., Adipose tissue-derived therapeutics. Expert Opin Biol Ther. Aug. 2003;3(5):705-13.

Seifert et al., An implanted hamster greene melanoma expressing multiple host-tissue differentiation. J Submicrosc Cytol Pathol. Jul. 2003;35(3):315-21.

Taguchi et al., Administration of CD34+ cells after stroke enhances neurogenesis via angiogenesis in a mouse model. J Clin Invest. Aug. 2004;114(3):330-8.

* cited by examiner

GENERATION AND USE OF VASCULOGENIC TUMORS AND PRODUCTS DERIVED FROM SAME

RELATED APPLICATIONS

This application claims benefit under 35 U.S.C. 119(e) of the filing date of U.S. Ser. No. 60/728,033 filed on Oct. 18, 2005, the entire disclosure of which is incorporated herein by reference.

GOVERNMENT SUPPORT

The present invention was supported in part by grants from the United States National Cancer Institute CA-78496 and CA-86302. The U.S. Government may retain certain rights in the invention.

FIELD OF THE INVENTION

The present invention relates generally to tissue regeneration.

BACKGROUND OF THE INVENTION

The therapeutic need to generate nerves, arteries and veins is enormous. Fifty-eight million people in the United States have cardiovascular disease (Ingham, P. W. et al, *Genes Devel.* 15, 3059-87 (2001)). Another quarter of a million people have spinal cord injuries. In addition, damage to peripheral nerves often results in loss of muscle function, impaired sensation, and painful neuropathies (Evans, G. R. *Semin. Surg. Oncol.* 19(3), 312-318 (2000)). Progress in addressing these pathologies has been mainly along two fronts—the graft and the bioengineered construct. At present, the "gold standard" in nerve and vessel replacement is still the autologous graft (Evans, G. R. *Semin. Surg. Oncol.* 19(3), 312-318 (2000)). Understanding how to harness and amplify the regenerative capacities of adult tissues stands to provide answers to many regeneration problems and augment bioengineering solutions (Fuchs, E. et al. *Cell* 116, 769-778 (2004). To this end, there is a great unmet need to provide mechanistic insight into development and to recover latent capacities for arteriogenic and neurogenic activity.

SUMMARY OF THE INVENTION

It is widely believed that, in order to obtain the oxygen and nutrient supply they need to survive, tumors invade surrounding tissues and generate a number of factors to stimulate an angiogenic program. It has now been discovered according to the present invention how to recapitulate the embryogenesis program in adult tissue, using tumors as a source of signals involved in directing tissue generation, including tissue regeneration. The invention is based in part on the surprising discovery by the inventors that a developing tumor can be utilized to elicit large-gauge neurovascular bundles, including nerves, arteries, and veins in a supporting fascial sheath, which reached up to 30 mm in length and homed to the tumor. The embryonic developmental morphogen Sonic hedgehog (Shh) (Lum, L. et al. *Science* 304, 1755-9 (2004); Chiang, C. et al., *Nature* 383, 407-13 (1996); Marti, E. et al., *Nature* 375, 322-325 (1995); Ingham, P. W. et al., *Genes Devel.* 15, 3059-87 (2001)) was detected throughout the neurovascular bundle and surrounding sheath and found to be essential for bundle induction.

The invention is based in part upon the surprising discovery by the inventors of the regenerative potential of the cellular components of arteries, veins, and nerves in a mature animal, and the ability of tumors to unlock this potential. The invention is also based in part upon the surprising demonstration by the inventors, using this discovery, of induction of neurovascular bundles of unprecedented scale. The invention is also based in part on the surprising discovery by the inventors of a critical role for Shh signaling in promoting these structures through a recapitulation of embryogenic fate determination and developmental programs.

It has been discovered according to the invention that following tumor implantation there can be a remodeling of the vascular hierarchy of the host, with the tumor acquiring a large-gauge vascular accommodation reminiscent of that to an organ. The confinement of influx to and efflux from the tumor to a coupled artery and vein is likened to that seen in encapsulated organs, e.g., the kidney. Strikingly, nerve induction accompanies the artery and vein, together forming a neurovascular bundle. The ability of a tumor to elicit directed arteriogenesis and neurogenesis in mature animals has ramifications for the exploitation of regenerative potential in the adult setting.

It has also been discovered according to the invention that the large vascular structures induced by the implanted tumor can be used to access information about tumor influx and tumor efflux. More particularly, the invention provides methods for identifying tumor products and for assessing tumor uptake and metabolism of various agents including drugs.

The invention in one aspect is a method for generating a tumor characterized by a vasculogenic program. The method according to this aspect of the invention includes the steps of implanting an intact tumor, or a nondispersed portion thereof, into a living vertebrate; and growing the implanted tumor or portion thereof in the vertebrate for at least a selected time, to generate a tumor characterized by a vasculogenic program. In one embodiment the steps of implanting and growing are repeated at least one time.

In one embodiment according to this and other aspects of the invention, the vasculogenic program comprises an artery and a vein.

In one embodiment according to this and other aspects of the invention, the intact tumor is a tumor characterized by a vasculogenic program.

In one embodiment according to this and other aspects of the invention, the intact tumor is derived from a tumor cell line.

In one embodiment according to this and other aspects of the invention, the implanting is implanting into a subcutaneous site.

In one embodiment according to this and other aspects of the invention, the implanting is implanting into a peritoneal site.

In one aspect the invention is a method for isolating a selected type of living tissue from a tumor. The method according to this aspect of the invention includes the steps of implanting an intact tumor, or a nondispersed portion thereof, into a living vertebrate; growing the implanted tumor or portion thereof in the vertebrate for at least a selected time, to generate a tumor characterized by a vasculogenic program; and isolating a selected type of living tissue from the tumor characterized by the vasculogenic program.

In one embodiment according to this and other aspects of the invention, the selected type of living tissue is selected from artery and vein.

In one embodiment according to this and other aspects of the invention, the selected type of living tissue is nerve.

In one embodiment according to this and other aspects of the invention, the selected type of living tissue is a stem cell.

In one aspect the invention is a composition comprising a selected type of living tissue prepared according to the method described above, namely, implanting an intact tumor, or a nondispersed portion thereof, into a living vertebrate; growing the implanted tumor or portion thereof in the vertebrate for at least a selected time, to generate a tumor characterized by a vasculogenic program; and isolating a selected type of living tissue from the tumor characterized by the vasculogenic program.

In one aspect the invention is a method for inducing host tissue regeneration. The method according to this aspect of the invention includes the steps of implanting an effective amount of an intact tumor, or a nondispersed portion thereof, into a vertebrate host in need of host tissue regeneration; and growing the implanted tumor or portion thereof in the vertebrate host for at least a selected time, to induce host tissue regeneration.

In one embodiment according to this and other aspects of the invention, the implanting is implanting into a site toward which direction regeneration is desired.

In one embodiment according to this and other aspects of the invention, the intact tumor, or the nondispersed portion thereof, is contained within a semipermeable membrane.

In one embodiment according to this and other aspects of the invention, the vertebrate host has vascular disease and the host tissue is artery.

In one embodiment according to this and other aspects of the invention, the vertebrate host has nerve disease and the host tissue is nerve.

In one embodiment according to this and other aspects of the invention, the nerve disease is peripheral nerve disease.

In one embodiment according to this and other aspects of the invention, the nerve disease is spinal cord injury.

In one aspect the invention is a method for inducing host tissue regeneration. The method according to this aspect of the invention includes the step of implanting an effective amount of a tumor product, wherein the tumor product is isolated from a tumor characterized by a vasculogenic program, into a vertebrate host in need of host tissue regeneration, to induce host tissue regeneration.

In one embodiment according to this and other aspects of the invention, the tumor product is selected from the group consisting of cytokines, growth factors, morphogens, angiogenesis factors, and anti-angiogenesis factors.

In one embodiment according to this and other aspects of the invention, the tumor product is a cell.

In one embodiment according to this and other aspects of the invention, the tumor product is contained within a semipermeable membrane.

The invention in one aspect is a method for inducing host tissue regeneration. The method according to this aspect of the invention includes the step of administering an effective amount of a tumor product, wherein the tumor product is isolated from a tumor characterized by a vasculogenic program, to a vertebrate host in need of host tissue regeneration, to induce host tissue regeneration.

In one aspect the invention is a method for identifying a tumor product. The method according to this aspect of the invention includes the steps of providing a tumor characterized by a vasculogenic program; sampling arterial influx to the tumor; sampling venous efflux from the tumor; measuring an amount of a composition in the influx; measuring an amount of the composition in the efflux; and identifying the composition as a tumor product when the amount of the composition in the efflux exceeds the amount of the composition in the influx.

In one aspect the invention is a method for isolating a tumor product. The method according to this aspect of the invention includes the steps of providing a tumor characterized by a vasculogenic program; sampling venous efflux from the tumor, wherein the efflux comprises a tumor product; and isolating the tumor product from the efflux.

In one aspect the invention is a method for analyzing uptake or metabolism of a composition by a tumor. The method according to this aspect of the invention includes the steps of providing a tumor characterized by a vasculogenic program; sampling arterial influx to the tumor; sampling venous efflux from the tumor; measuring an amount of a composition, or a metabolite thereof, in the influx; measuring an amount of the composition, or the metabolite thereof, in the efflux; and comparing the amount of the composition, or the metabolite thereof, in the influx to the amount of the composition, or the metabolite thereof, in the efflux.

In one embodiment according to this aspect of the invention, the composition is a cell.

In one embodiment according to this aspect of the invention, the composition is a drug.

In one embodiment according to this aspect of the invention, the composition or the metabolite thereof in the influx is a drug and wherein the composition or the metabolite thereof in the efflux is a metabolite of the drug.

In one embodiment according to this aspect of the invention, the composition or the metabolite thereof in the influx is a metabolite of a drug and wherein the composition or the metabolite thereof in the efflux is the metabolite of the drug.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving," and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

DETAILED DESCRIPTION OF THE INVENTION

Figure 1A:
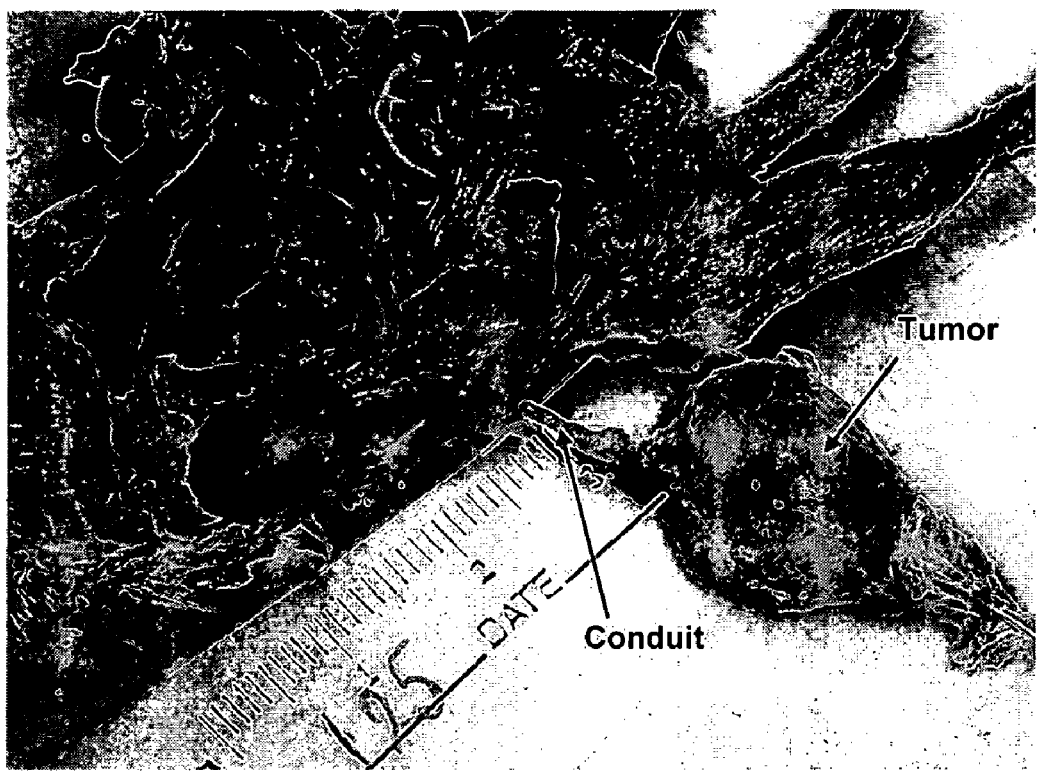
FIGS. 1A, B and C are photographic images showing that implanted tumor elicited large-gauge arteries and veins which linked them to host vasculature. A) A severe combined immunodeficiency (SCID) mouse with a liposarcoma xenograft implanted low on the back was injected with orange latex casting through the left ventricle to identify the arterial network. The tumor, 1.78×1.26 cm at the time of sacrifice, is seen to be well delimited, similar to an organ. A significant artery is seen to connect the tumor to the host. It connects to the aorta at the level of the renal arterial branches. The artery is seen to branch before entering the tumor. Orange color on the mouse surface (including hair) represents latex casting transfer due to handling. B) A vascular conduit as it appears when the skin containing the tumor mass is dissected to the right. The fascia in the vicinity of the conduit is flexible, and the conduit appeared somewhat serpentine in its relaxed position. Here it is shown pulled taut to the right by forceps. The conduit extends from the junction with the tumor (shown by the arrow), leftwards along the back to a point of entry into the abdomen concealed by the skin flap on the left. C) The surgically trimmed clear fibro-adipose sheath, and the distinct artery (red) and vein (dark red) contained within it. This fascial bridge between the abdomen and the fascia abutting the skin appears only in tumor-bearing mice and has no analog in control mice.

The neurovascular system, a hierarchical structure comprised of a network of large and small nerves and vessels, is established during embryogenesis. The neurovascular map in mature animals is essentially determined, although locally perturbable through injury or disease. It has now been demonstrated according to the invention that following tumor implantation there can be a remodeling of the vascular hierarchy of the host, with the tumor acquiring a large-gauge vascular accommodation reminiscent of that to an organ. The confinement of influx to and efflux from the tumor to a coupled artery and vein is likened to that seen in encapsulated organs, e.g. the kidney. Strikingly, nerve induction accompanies the artery and vein, together forming a neurovascular bundle. The ability of a tumor to elicit directed arteriogenesis and neurogenesis in mature animals has ramifications for the exploitation of regenerative potential in the adult setting.

Reasoning that since a tumor consists of a heterogeneous, unstable cell population that is poised to rapidly respond to ambient selection pressures (Kinzler, K. W. et al., *Cell* 87, 159-170 (1996); Folkman, J. et al., *Nature Revs. Molec. Cell Biol.* 1, 76-79 (2000)) and to redirect the local environment in a way that meets its own needs, it has been discovered according to the invention that one can channel this capacity to useful biological ends. Inadequate oxygen and nutrient supply is a basic constraint to tumor growth that elicits compensatory responses within the tumor population (e.g., upregulation of angiogenic cytokines) that induce neovascularization in the local environment. Additionally, the tumor's unstable genome contains genetically varied clones, with selection favoring those clones whose chance expressions promote tumor expansion, including more effective nutrient support (Folkman, J. et al., *Nature Revs. Molec. Cell Biol.* 1, 76-79 (2000); Hanahan, D. et al., *Cell* 100, 57-70 (2000)). Owing to such dynamics, the tumor in effect represents an efficient "problem solving machine" for those physiological problems whose solutions are tied, or can be made to be tied, to promoting tumor expansion. The underlying process is thus analogous to the Monte Carlo method (Rubinstein, R. Y., Wiley. New York (1981)) employed computationally to discover by stochastics optimum solutions to otherwise intractable dynamical problems. Clearly, tumor-directed arteriogenesis is a solution to the problem of nutrient acquisition, particularly in instances where significant nutrient delivery to a tumor is required while, at the same time, multiple smaller vessels are discouraged. Accordingly, it has now been discovered according to the invention that if a tumor is physically constrained to be more insulated from its surround, the arteriogenesis "solution" is more favored, as is seen in organs.

The fundamental biological constraint that tumors need sufficient vasculature to expand (Folkman, J. et al, *Nature Revs. Molec. Cell Biol.* 1, 76-79 (2000)) was at the root of the experiments described in the Examples below to go beyond angiogenesis and utilize tumors to promote arteriogenesis. As described in greater detail below, it was surprisingly discovered that not only can developing tumors be used to induce arteriogenesis, but also that the induced arteriogenesis was accompanied by induced neurogenesis.

While there are no previous reports of tumors inducing neurogenesis, and there is no direct rationale for the induction of nerves by tumors, there is sufficient evidence to suggest that neurogenesis and arteriogenesis are closely coupled. In the body plan of all vertebrates the occurrence of large vessels is accompanied by nerves. Pioneering work by Martin and Lewis (Martin, P. et al., *Int. J Dev. Biol.* 33(3), 379-387 (1989)) concluded that peripheral nerves and blood vessels follow the same route because they respond independently to the same mesenchymal cues. Furthermore, cell components of both nerves and vessels are known to respond to some of the same cytokines, e.g., ephrins/Eph (Shima, D. T. et al., *Curr. Opin. Genet. Dev.* 10(5), 536-542 (2000)). Platelet derived growth factor (PDGF) and transforming growth factor beta (TGF-beta) are mitogenic for both Schwann cells and for vascular smooth muscle cells. These are two of an increasing list of growth factors that have both neurogenic and angiogenic effects (Fu, S. Y. et al., *Molec. Neurobiol.* 14(1-2), 67-116 (1997); Nomi, M. et al., *Molec. Aspects Med.* 23(6), 463-483 (2002)). Following peripheral nerve injury, the angiogenic molecules vascular endothelial growth factor (VEGF), and fibroblast growth factors aFGF and bFGF, promote axon regeneration (Fu, S. Y. et al., *Molec. Neurobiol.* 14(1-2), 67-116 (1997); Sondell, M. et al., *Eur. J Neurosci.* 12(12), 4243-4254 (2000); Fujimoto, E. et al., *J. Neurocytol.* 26(8), 511-528 (1997)). Neuropilin-1, a mediator of neuronal guidance, is also a specific receptor of VEGF165 (Soker, S. et al., *Cell* 92(6), 735-745 (1998)). More recently, it was reported that sensory nerves determine the patterning of arterial differentiation in developing chick skin, presumably mediated by VEGF (Mukouyama, Y. S. et al., *Cell* 109(6), 693-705 (2002)).

The embryonic developmental morphogen Sonic hedgehog (Shh) (Lum, L. et al., *Science* 304, 1755-9 (2004); Chiang, C. et al., *Nature* 383, 407-13 (1996); Marti, E. et al., A.P., *Nature* 375, 322-325 (1995); Ingham, P. W. et al., *Genes Devel.* 15, 3059-87 (2001)) was found to be instrumental in tumor-driven adult neurogenesis and essential for bundle induction.

The invention in certain aspects relates to a method for generating a tumor characterized by a vasculogenic program. As used herein, a vasculogenic program refers to a set of biochemical steps implemented by a given tumor to induce de novo new arteries and veins characterized by the presence of smooth muscle. A described herein, a vasculogenic program can also induce de novo new nerves and/or neurovascular bundles. This vasculogenic program includes for example the expression of appropriate factors to induce and effectuate arteriogenesis and/or neurogenesis. Such factors can include a morphogen, including in particular Sonic hedgehog. Such factors can be cytokines, e.g. ephrins/Eph, platelet-derived growth factor (PDGF), transforming growth factor beta (TGF-beta), vascular endothelial growth factor (VEGF), fibroblast growth factors aFGF and bFGF, and neuropilin-1.

As used-herein, a tumor characterized by a vasculogenic program is a tumor that has the capacity to carry out such a program, i.e., a tumor that can and does promote arteriogenesis and neurogenesis and can effectuate the generation of directed arteries, veins, nerves, and/or neurovascular bundles. A tumor characterized by a vasculogenic program generally exhibits, by its anatomy or by tumor products generated by the tumor, the tumor's ability to induce the formation of arteries, veins, nerves, and/or neurovascular bundles.

As used herein, an artery refers to a tubular vascular structure, other than a capillary, having concentric layers of endothelium, internal elastic lamina, and smooth muscle as recognized by those of skill in the art. Arteries include arterioles, small arteries, muscular arteries, and large elastic arteries. Arteries normally transport blood away from the heart. In one embodiment an artery has an external diameter of at least 1 mm.

As used herein, a vein refers to a tubular vascular structure, other than a capillary, having concentric layers of endothelium and smooth muscle, as recognized by those of skill in the art. Veins include venules, veins of small caliber, veins of medium caliber, and veins of large caliber. Veins normally transport blood toward the heart. In one embodiment a vein has an external diameter of at least 1 mm.

A vasculogenic program includes an arteriogenic program. An arteriogenic program, as used herein, is a type of vasculogenic program that is specifically involved in inducing arteries.

A vasculogenic program is to be distinguished from an angiogenic program. As used herein, an angiogenic program refers to a set of biochemical steps implemented by a given tumor to induce sprouting of capillaries from pre-existing arteries and veins near or adjacent to the tumor, to penetrate into the tumor. The capillaries arising from an angiogenic program are essentially free of smooth muscle and thus are composed essentially of naked endothelial cells.

Various aspects of the invention include the step of implanting an intact tumor, or a nondispersed portion thereof, into a living vertebrate. As used herein, a tumor refers to a mass of abnormally replicating cells of vertebrate origin. Abnormally replicating cells of a tumor are termed tumor cells or, equivalently, cancer cells. A subject having a tumor is a subject in which a detectable tumor is present. Tumors include but are not limited to cancers of the biliary tract; bladder; bone; brain; breast; cervix; colon; endometrium; esophagus; heart; kidney; larynx; liver; lung (e.g., small cell and non-small cell); meninges; oral cavity (including any of lip, tongue, mouth, pharynx); ovary; pancreas; prostate; rectum; skeletal muscle; skin; small intestine; spinal cord; stomach; testis; thyroid; ureter; uterus; as well as choriocarcinoma; intraepithelial neoplasms; leukemias; lymphomas; melanoma; neuroblastoma; retinoblastoma; sarcomas; and other carcinomas and sarcomas. In one embodiment the tumor is a solid tumor that excludes leukemias and other hematologic cancers. Tumors include both primary and metastatic tumors.

An intact tumor can be derived from any suitable source. In one embodiment the intact tumor is derived from a spontaneously occurring tumor in a vertebrate subject. For example, a biopsied or surgically removed tumor obtained from a human subject can be used as an intact tumor. In one embodiment the intact tumor is derived from a tumor cell line. Tumor cell lines are well known in the art and many are available from commercial sources. Example of tumor cell lines include, without limitation, those listed in Table 1, available from American Type Culture Collection (ATCC, Manassas, Va.).

TABLE 1

Exemplary Tumor Cell Lines

| ATCC No. | Name | Cancer Type | Tissue Source |
|---|---|---|---|
| CRL-2327 | HCC1428 | adenocarcinoma | breast |
| CRL-7850 | Hs 588.T | adenocarcinoma | cervix |
| CCL-249 | NCI-H548 | adenocarcinoma | colon |
| CRL-5972 | SNU-C1 | adenocarcinoma | colon |
| CRL-7207 | Hs 241.T | adenocarcinoma | colon |
| CRL-7213 | Hs 255.T | adenocarcinoma | colon |
| CRL-7435 | Hs 698.T | adenocarcinoma | colon |
| HTB-78 | SW 626 | adenocarcinoma | colon; ovary metastasis |
| CRL-7928 | HuTu 80 | adenocarcinoma | duodenum |
| HTB-40 | HuTu 80 | adenocarcinoma | duodenum |
| HTB-111 | AN3 CA | adenocarcinoma | endometrial cancer; lymph node metastasis |
| CRL-7911 | A704 | adenocarcinoma | kidney |
| HTB-45 | A-704 | adenocarcinoma | kidney |
| HTB-49 | SW 839 | adenocarcinoma | kidney; clear cell |
| CRL-5892 | NCI-H1755 | adenocarcinoma | liver |
| HTB-52 | SK-HEP-1 | adenocarcinoma | liver; ascites |
| CRL-5944 | NCI-H2405 | adenocarcinoma | lung |
| CRL-5844 | NCI-H838 | adenocarcinoma | lung |
| CRL-5866 | NCI-H1373 | adenocarcinoma | lung |
| CRL-5868 | NCI-H1395 | adenocarcinoma | lung |
| CRL-5918 | NCI-H2073 | adenocarcinoma | lung |
| CRL-5942 | NCI-H2347 | adenocarcinoma | lung |
| CRL-7380 | Hs 618.T | adenocarcinoma | lung |
| CRL-5877 | NCI-H1573 | adenocarcinoma | lung |
| CRL-5907 | NCI-H1944 | adenocarcinoma | lung |
| HTB-57 | SK-LU-1 | adenocarcinoma | lung |
| CRL-5850 | NCI-H920 | adenocarcinoma | lung, lymph node metastasis |
| CRL-5852 | NCI-H969 | adenocarcinoma | lung, pleural effusion |
| CRL-5865 | NCI-H1355 | adenocarcinoma | lung, pleural effusion |
| CRL-5872 | NCI-H1437 | adenocarcinoma | lung, pleural effusion |
| CRL-5876 | NCI-H1568 | adenocarcinoma | lung; lymph node metastasis |
| CRL-5881 | NCI-H1623 | adenocarcinoma | lung; lymph node metastasis |
| CRL-5882 | NCI-H1648 | adenocarcinoma | lung; lymph node metastasis |
| CRL-5887 | NCI-H1693 | adenocarcinoma | lung; lymph node metastasis |
| CRL-5897 | NCI-H1819 | adenocarcinoma | lung; lymph node metastasis |
| CRL-5909 | NCI-H1993 | adenocarcinoma | lung; lymph node metastasis |
| CRL-5911 | NCI-H2009 | adenocarcinoma | lung; lymph node metastasis |
| CRL-5912 | NCI-H2023 | adenocarcinoma | lung; lymph node metastasis |
| CRL-5922 | NCI-H2087 | adenocarcinoma | lung; lymph node metastasis |
| CRL-5936 | NCI-H2250 | adenocarcinoma | lung; lymph node metastasis |
| CRL-5895 | NCI-H1792 | adenocarcinoma | lung; pleural effusion |
| CRL-5985 | NCI-H2122 | adenocarcinoma | lung; pleural effusion |
| HTB-179 | NCI-H676B | adenocarcinoma | lung; pleural effusion |
| HTB-55 | Calu-3 | adenocarcinoma | lung; pleural effusion |
| CRL-5889 | NCI-H1703 | adenocarcinoma | lung; squamous cell |
| CRL-2351 | AU565 | adenocarcinoma | mammary gland; breast |
| CRL-7222 | Hs 274.T | adenocarcinoma | mammary gland; breast |

TABLE 1-continued

Exemplary Tumor Cell Lines

| ATCC No. | Name | Cancer Type | Tissue Source |
|---|---|---|---|
| CRL-7226 | Hs 280.T | adenocarcinoma | mammary gland; breast |
| CRL-7227 | Hs 281.T | adenocarcinoma | mammary gland; breast |
| CRL-7245 | Hs 343.T | adenocarcinoma | mammary gland; breast |
| CRL-7253 | Hs 362.T | adenocarcinoma | mammary gland; breast |
| CRL-7477 | Hs 739.T | adenocarcinoma | mammary gland; breast |
| CRL-7480 | Hs 741.T | adenocarcinoma | mammary gland; breast |
| CRL-7647 | Hs 902.T | adenocarcinoma | mammary gland; breast |
| HTB-132 | MDA-MB-468 | adenocarcinoma | mammary gland; breast |
| HTB-27 | MDA-MB-361 | adenocarcinoma | mammary gland; breast |
| HTB-30 | SK-BR-3 | adenocarcinoma | mammary gland; breast; malignant pleural effusion |
| HTB-128 | MDA-MB-415 | adenocarcinoma | mammary gland; breast; pleural effusion |
| HTB-130 | MDA-MB-436 | adenocarcinoma | mammary gland; breast; pleural effusion |
| HTB-21 | CAMA-1 | adenocarcinoma | mammary gland; breast; pleural effusion |
| HTB-22 | MCF7 | adenocarcinoma | mammary gland; breast; pleural effusion |
| HTB-26 | MDA-MB-231 | adenocarcinoma | mammary gland; breast; pleural effusion |
| HTB-151 | Hs 696 | adenocarcinoma | metastasis to bone (sacrum) |
| HTB-147 | Hs 700T | adenocarcinoma | metastasis to the pelvis |
| CRL-10303 | MDAH 2774 | adenocarcinoma | ovary |
| HTB-161 | NIH:OVCAR-3 | adenocarcinoma | ovary |
| HTB-75 | Caov-3 | adenocarcinoma | ovary |
| HTB-76 | Caov-4 | adenocarcinoma | ovary |
| HTB-77 | SK-OV-3 | adenocarcinoma | ovary; ascites |
| CRL-1687 | BxPC-3 | adenocarcinoma | pancreas |
| CRL-1997 | HPAF-II | adenocarcinoma | pancreas |
| CRL-2119 | HPAC | adenocarcinoma | pancreas |
| CRL-2172 | SW 1990 | adenocarcinoma | pancreas |
| HTB-79 | Capan-1 | adenocarcinoma | pancreas |
| HTB-80 | Capan-2 | adenocarcinoma | pancreas |
| CRL-1682 | AsPC-1 | adenocarcinoma | pancreas; ascites |
| CRL-1435 | PC-3 | adenocarcinoma | prostate |
| CRL-2422 | MDA PCa 2b | adenocarcinoma | prostate |
| CCL-235 | SW837 | adenocarcinoma | rectum |
| CRL-1622 | KLE | adenocarcinoma | uterus; endometrium |
| HTB-112 | HEC-1-A | adenocarcinoma | uterus; endometrium |
| HTB-113 | HEC-1-B | adenocarcinoma | uterus; endometrium |
| CRL-7758 | TE 206.T | adenocarcinoma | unknown |
| CRL-5883 | NCI-H1650 | adenocarcinoma | bronchoalveolar carcinoma lung; pleural effusion |
| CRL-5885 | NCI-H1666 | adenocarcinoma | bronchoalveolar carcinoma lung; pleural effusion |
| CRL-5894 | NCI-H1781 | adenocarcinoma | bronchoalveolar carcinoma lung; pleural effusion |
| CRL-2220 | CA-HPV-10 | adenocarcinoma | prostate |
| CRL-5800 | NCI-H23 | adenocarcinoma | non-small cell lung cancer lung |
| CRL-5810 | NCI-H522 | adenocarcinoma | non-small cell lung cancer lung |
| CRL-5870 | NCI-H1435 | adenocarcinoma | non-small cell lung cancer lung |
| CRL-5875 | NCI-H1563 | adenocarcinoma | non-small cell lung cancer lung |
| CRL-5884 | NCI-H1651 | adenocarcinoma | non-small cell lung cancer lung |
| CRL-5891 | NCI-H1734 | adenocarcinoma | non-small cell lung cancer lung |
| CRL-5896 | NCI-H1793 | adenocarcinoma | non-small cell lung cancer lung |
| CRL-5899 | NCI-H1838 | adenocarcinoma | non-small cell lung cancer lung |
| CRL-5908 | NCI-H1975 | adenocarcinoma | non-small cell lung cancer lung |
| CRL-5914 | NCI-H2030 | adenocarcinoma | non-small cell lung cancer lung |
| CRL-5921 | NCI-H2085 | adenocarcinoma | non-small cell lung cancer lung |
| CRL-5935 | NCI-H2228 | adenocarcinoma | non-small cell lung cancer lung |
| CRL-5939 | NCI-H2291 | adenocarcinoma | non-small cell lung cancer lung |
| CRL-5941 | NCI-H2342 | adenocarcinoma | non-small cell lung cancer lung |
| CRL-5834 | NCI-H647 | adenosquamous carcinoma | lung; pleural effusion; mixed |
| HTB-178 | NCI-H596 | adenosquamous carcinoma | lung |
| CRL-10296 | NCI-H295 | adrenocortical carcinoma | adrenal gland, cortex |
| CRL-2170 | SW 1573 | alveolar cell carcinoma | lung |
| CRL-1579 | C32TG | amelanotic melanoma | skin |
| CRL-1585 | C32 | amelanotic melanoma | skin |
| HTB-137 | Hs 695T | amelanotic melanoma | metastasis to lymph node |
| CRL-9267 | W5-6 | anaplastic carcinoma | unknown, probably lung |
| HTB-56 | Calu-6 | anaplastic carcinoma | unknown, probably lung |
| CRL-2461 | SV7tert | angiomyolipoma | kidney |
| CRL-1718 | CCF-STTG1 | astrocytoma | brain |
| HTB-12 | SW 1088 | astrocytoma | brain |

TABLE 1-continued

Exemplary Tumor Cell Lines

| ATCC No. | Name | Cancer Type | Tissue Source |
| --- | --- | --- | --- |
| HTB-13 | SW 1783 | astrocytoma | brain |
| CRL-7762 | TE 354.T | basal cell carcinoma | skin |
| CRL-7646 | Hs 900.T | benign osteoid osteoma | bone |
| CRL-7649 | Hs 903.T | benign osteoid osteoma | bone |
| CRL-7672 | Hs 919.T | benign osteoid osteoma | bone |
| CRL-2081 | MSTO-211H | biphasic mesothelioma | metastasis to lung |
| CRL-7588 | Hs 853.T | bladder carcinoma | metastasis to lung or bronchus |
| CRL-2294 | BCP-1 | body cavity based lymphoma | peripheral blood; B lymphoblast |
| CRL-5807 | NCI-H358 | bronchioalveolar carcinoma | lung; bronchiole; alveolus |
| CRL-5835 | NCI-H650 | bronchioalveolar carcinoma | lung |
| CRL-7194 | Hs 229.T | bronchogenic adenocarcinoma | lung |
| HTB-168 | ChaGo-K-1 | bronchogenic carcinoma | lung; bronchus |
| CRL-1647 | ST486 | Burkitt's lymphoma | ascites; B lymphocyte |
| HTB-62 | P3HR-1 | Burkitt's lymphoma | ascites; B lymphocyte |
| CCL-85 | EB-3 | Burkitt's lymphoma | B lymphocyte |
| CCL-86 | Raji | Burkitt's lymphoma | B lymphocyte |
| CCL-87 | Jiyoye | Burkitt's lymphoma | B lymphocyte |
| CRL-1432 | NAMALWA | Burkitt's lymphoma | B lymphocyte |
| CRL-1484 | HS-Sultan | Burkitt's lymphoma | B lymphocyte |
| CRL-1648 | CA46 | Burkitt's lymphoma | B lymphocyte |
| CRL-2392 | GA-10 | Burkitt's lymphoma | B lymphocyte |
| CRL-2393 | GA-10 | Burkitt's lymphoma | B lymphocyte |
| CRL-2394 | GA-10 | Burkitt's lymphoma | B lymphocyte |
| HTB-61 | EB2 | Burkitt's lymphoma | B lymphocyte |
| CRL-7933 | P-3J | Burkitt's lymphoma | lymph node; B lymphoblast |
| CRL-7936 | Raji | Burkitt's lymphoma | lymph node; B lymphoblast |
| CRL-10237 | 2F7 | Burkitt's lymphoma | lymph node; B lymphocyte |
| CCL-213 | Daudi | Burkitt's lymphoma | peripheral blood; B lymphoblast |
| CCL-214 | NC-37 | Burkitt's lymphoma | peripheral blood; B lymphoblast |
| HTB-60 | EB1 | Burkitt's lymphoma | upper maxilla; B lymphocyte |
| CRL-1596 | Ramos | Burkitt's lymphoma (American) | B lymphocyte |
| CRL-1923 | Ramos | Burkitt's lymphoma (American) | B lymphocyte |
| CRL-2128 | NCI-H295R | carcinoma | adrenal gland, cortex |
| CRL-1594 | C-4I | carcinoma | cervix |
| CRL-1595 | C-4 II | carcinoma | cervix |
| CRL-7396 | Hs 636.T | carcinoma | cervix |
| CRL-7914 | C4II | carcinoma | cervix |
| CRL-7920 | DoTc2 4510 | carcinoma | cervix |
| HTB-31 | C-33 A | carcinoma | cervix |
| HTB-32 | HT-3 | carcinoma | cervix |
| CRL-7908 | A498 | carcinoma | kidney |
| HTB-44 | A-498 | carcinoma | kidney |
| CCL-185 | A549 | carcinoma | lung |
| HTB-53 | A-427 | carcinoma | lung |
| CRL-5867 | NCI-H1385 | carcinoma | lymph node; squamous cell |
| CRL-7316 | Hs 540.T | carcinoma | mammary gland; breast |
| CRL-7336 | Hs 566(B).T | carcinoma | mammary gland; breast |
| CRL-7365 | Hs 605.T | carcinoma | mammary gland; breast |
| CRL-7368 | Hs 606 | carcinoma | mammary gland; breast |
| CRL-7721 | MB 157 | carcinoma | mammary gland; breast; pleural effusion |
| CRL-1420 | MIA PaCa-2 | carcinoma | pancreas |
| HTB-134 | Hs 766T | carcinoma | pancreas |
| CCL-138 | Detroit 562 | carcinoma | pharynx |
| CRL-10995 | LNCaP-FGC | carcinoma | prostate |
| CRL-1740 | LNCaP clone FGC | carcinoma | prostate |
| CRL-2505 | 22Rv1 | carcinoma | prostate |
| HTB-81 | DU 145 | carcinoma | prostate |
| CRL-5833 | NCI-H630 | carcinoma | rectum |
| CRL-7870 | Hs 740.T | carcinoma | stomach |
| CRL-1803 | TT | carcinoma | thyroid, medulla |
| CRL-1472 | HT-1376 | carcinoma | urinary bladder |
| CRL-1473 | HT-1197 | carcinoma | urinary bladder |
| CRL-7150 | Hs 195.T | carcinoma | urinary bladder |
| CRL-7193 | Hs 228.T | carcinoma | urinary bladder |
| CRL-7833 | Hs 172.T | carcinoma | urinary bladder |
| CRL-7926 | HT 1197.T | carcinoma | urinary bladder |
| CRL-7927 | HT 1376.T | carcinoma | urinary bladder |
| HTB-9 | 5637 | carcinoma | urinary bladder |
| CRL-1671 | RL95-2 | carcinoma | uterus; endometrium |
| HTB-118 | SW 962 | carcinoma | vulva |
| CCL-257 | NCI-H1688 | carcinoma; classic small cell lung cancer | lung |

TABLE 1-continued

Exemplary Tumor Cell Lines

| ATCC No. | Name | Cancer Type | Tissue Source |
|---|---|---|---|
| CRL-5804 | NCI-H187 | carcinoma; classic small cell lung cancer | lung |
| CRL-5808 | NCI-H378 | carcinoma; classic small cell lung cancer | lung |
| CRL-5817 | NCI-H889 | carcinoma; classic small cell lung cancer | lung |
| CRL-5821 | NCI-H60 | carcinoma; classic small cell lung cancer | lung; pleural effusion |
| CRL-5825 | NCI-H220 | carcinoma; classic small cell lung cancer | lung; pleural effusion |
| CRL-5828 | NCI-H250 | carcinoma; classic small cell lung cancer | lung |
| CRL-5832 | NCI-N592 | carcinoma; classic small cell lung cancer | lung |
| CRL-5836 | NCI-H711 | carcinoma; classic small cell lung cancer | lung |
| CRL-5837 | NCI-H719 | carcinoma; classic small cell lung cancer | lung |
| CRL-5840 | NCI-H740 | carcinoma; classic small cell lung cancer | lung |
| CRL-5841 | NCI-H748 | carcinoma; classic small cell lung cancer | lung |
| CRL-5842 | NCI-H774 | carcinoma; classic small cell lung cancer | lung; soft tissue |
| CRL-5846 | NCI-H847 | carcinoma; classic small cell lung cancer | lung; pleural effusion |
| CRL-5849 | NCI-H865 | carcinoma; classic small cell lung cancer | lung; pleural effusion |
| CRL-5854 | NCI-H1059 | carcinoma; classic small cell lung cancer | lung |
| CRL-5855 | NCI-H1092 | carcinoma; classic small cell lung cancer | lung |
| CRL-5856 | NCI-H1105 | carcinoma; classic small cell lung cancer | lung |
| CRL-5861 | NCI-H1284 | carcinoma; classic small cell lung cancer | lung |
| CRL-5862 | NCI-H1304 | carcinoma; classic small cell lung cancer | lung; pleural effusion |
| CRL-5869 | NCI-H1417 | carcinoma; classic small cell lung cancer | lung |
| CRL-5871 | NCI-H1436 | carcinoma; classic small cell lung cancer | lung |
| CRL-5886 | NCI-H1672 | carcinoma; classic small cell lung cancer | lung |
| CRL-5888 | NCI-H1694 | carcinoma; classic small cell lung cancer | lung |
| CRL-5898 | NCI-H1836 | carcinoma; classic small cell lung cancer | lung |
| CRL-5902 | NCI-H1876 | carcinoma; classic small cell lung cancer | lung |
| CRL-5906 | NCI-H1930 | carcinoma; classic small cell lung cancer | lung |
| CRL-5910 | NCI-H1994 | carcinoma; classic small cell lung cancer | lung |
| CRL-5916 | NCI-H2059 | carcinoma; classic small cell lung cancer | lung |
| CRL-5920 | NCI-H2081 | carcinoma; classic small cell lung cancer | lung; pleural effusion |
| CRL-5979 | NCI-H1339 | carcinoma; classic small cell lung cancer | lung; pleural effusion |
| CRL-5824 | NCI-H211 | carcinoma; small cell lung cancer | bone marrow |
| CRL-2049 | DMS 79 | carcinoma; small cell lung cancer | lung |
| CRL-2062 | DMS 53 | carcinoma; small cell lung cancer | lung |
| CRL-2064 | DMS 153 | carcinoma; small cell lung cancer | lung |
| CRL-2066 | DMS 114 | carcinoma; small cell lung cancer | lung |
| CRL-2177 | SW 1271 | carcinoma; small cell lung cancer | lung |
| CRL-2195 | SHP-77 | carcinoma; small cell lung cancer | lung; large cell, variant |

TABLE 1-continued

Exemplary Tumor Cell Lines

| ATCC No. | Name | Cancer Type | Tissue Source |
|---|---|---|---|
| CRL-5853 | NCI-H1048 | carcinoma; small cell lung cancer | lung; pleural effusion |
| CRL-5858 | NCI-H1184 | carcinoma; small cell lung cancer | lung; lymph node metastasis |
| CRL-5859 | NCI-H1238 | carcinoma; small cell lung cancer | lung |
| CRL-5864 | NCI-H1341 | carcinoma; small cell lung cancer | lung |
| CRL-5874 | NCI-H1522 | carcinoma; small cell lung cancer | lung; pleural effusion |
| CRL-5879 | NCI-H1618 | carcinoma; small cell lung cancer | lung |
| CRL-5901 | NCI-H1870 | carcinoma; small cell lung cancer | lung |
| CRL-5903 | NCI-H1882 | carcinoma; small cell lung cancer | lung |
| CRL-5905 | NCI-H1926 | carcinoma; small cell lung cancer | lung; lymph node metastasis |
| CRL-5913 | NCI-H2029 | carcinoma; small cell lung cancer | lung; lymph node metastasis |
| CRL-5927 | NCI-H2141 | carcinoma; small cell lung cancer | lung; lymph node metastasis |
| CRL-5929 | NCI-H2171 | carcinoma; small cell lung cancer | lung; pleural effusion |
| CRL-5931 | NCI-H2195 | carcinoma; small cell lung cancer | lung |
| CRL-5932 | NCI-H2196 | carcinoma; small cell lung cancer | lung |
| CRL-5933 | NCI-H2198 | carcinoma; small cell lung cancer | lung; lymph node metastasis |
| CRL-5934 | NCI-H2227 | carcinoma; small cell lung cancer | lung |
| CRL-5940 | NCI-H2330 | carcinoma; small cell lung cancer | lung; lymph node metastasis |
| CRL-5976 | NCI-H64 | carcinoma; small cell lung cancer | lung |
| CRL-5978 | NCI-H735 | carcinoma; small cell lung cancer | lung |
| CRL-5982 | NCI-H1963 | carcinoma; small cell lung cancer | lung |
| CRL-5983 | NCI-H2107 | carcinoma; small cell lung cancer | lung |
| CRL-5984 | NCI-H2108 | carcinoma; small cell lung cancer | lung |
| HTB-119 | NCI-H69 | carcinoma; small cell lung cancer | lung |
| HTB-120 | NCI-H128 | carcinoma; small cell lung cancer | lung; pleural effusion |
| HTB-171 | NCI-H446 | carcinoma; small cell lung cancer | lung; pleural effusion |
| HTB-172 | NCI-H209 | carcinoma; small cell lung cancer | lung |
| HTB-173 | NCI-H146 | carcinoma; small cell lung cancer | lung; pleural effusion |
| HTB-175 | NCI-H82 | carcinoma; small cell lung cancer | lung; pleural effusion |
| HTB-180 | NCI-H345 | carcinoma; small cell lung cancer | lung |
| CRL-5813 | NCI-H660 | carcinoma; small cell lung cancer; extrapulmonary origin | prostate; neuroendocrine |
| HTB-184 | NCI-H510A | carcinoma; small cell lung cancer; extrapulmonary origin | lung |
| CRL-11351 | H69AR | carcinoma; small cell lung cancer; multidrug resistant | lung |
| CRL-5809 | NCI-N417 | carcinoma; variant small cell lung cancer | lung |
| CRL-5811 | NCI-H526 | carcinoma; variant small cell lung cancer | lung |
| CRL-5823 | NCI-H196 | carcinoma; variant small cell lung cancer | lung |
| CRL-5831 | NCI-H524 | carcinoma; variant small cell lung cancer | lung; lymph node metastasis |

TABLE 1-continued

Exemplary Tumor Cell Lines

| ATCC No. | Name | Cancer Type | Tissue Source |
|---|---|---|---|
| CRL-5845 | NCI-H841 | carcinoma; variant small cell lung cancer | lung; lymph node metastasis |
| HTB-177 | NCI-H460 | carcinoma; large cell lung cancer | lung; pleural effusion |
| HTB-183 | NCI-H661 | carcinoma; large cell lung cancer | lung |
| CCL-256 | NCI-H2126 | carcinoma; non-small cell lung cancer | lung |
| CRL-5803 | NCI-H1299 | carcinoma; non-small cell lung cancer | lung; large cell; neuroendocrine |
| CRL-5816 | NCI-H810 | carcinoma; non-small cell lung cancer | lung; large cell; neuroendocrine |
| CRL-5818 | NCI-H1155 | carcinoma; non-small cell lung cancer | lung; large cell; neuroendocrine |
| CRL-7891 | Hs 819.T | chondrosarcoma | bone |
| HTB-94 | SW 1353 | chondrosarcoma | bone |
| CCL-98 | BeWo | choriocarcinoma | placenta |
| CRL-7394 | Hs 630.T | choriocarcinoma | placenta |
| HTB-144 | JAR | choriocarcinoma | placenta |
| HTB-36 | JEG-3 | choriocarcinoma | placenta |
| CRL-1978 | ES-2 | clear cell carcinoma | ovary |
| HTB-46 | Caki-1 | clear cell carcinoma | kidney |
| HTB-47 | Caki-2 | clear cell carcinoma | kidney |
| CCL-251 | NCI-H716 | colorectal adenocarcinoma | cecum |
| CCL-252 | NCI-H747 | colorectal adenocarcinoma | cecum |
| CCL-253 | NCI-H508 | colorectal adenocarcinoma | cecum |
| CCL-254 | NCI-H498 | colorectal adenocarcinoma | cecum |
| CCL-218 | WiDr | colorectal adenocarcinoma | colon |
| CCL-220 | COLO 320DM | colorectal adenocarcinoma | colon |
| CCL-220.1 | COLO 320HSR | colorectal adenocarcinoma | colon |
| CCL-221 | DLD-1 | colorectal adenocarcinoma | colon |
| CCL-222 | COLO 205 | colorectal adenocarcinoma | colon |
| CCL-224 | COLO 201 | colorectal adenocarcinoma | colon |
| CCL-225 | HCT-15 | colorectal adenocarcinoma | colon |
| CCL-227 | SW620 | colorectal adenocarcinoma | colon |
| CCL-228 | SW480 | colorectal adenocarcinoma | colon |
| CCL-229 | LoVo | colorectal adenocarcinoma | colon |
| CCL-230 | SW403 | colorectal adenocarcinoma | colon |
| CCL-231 | SW48 | colorectal adenocarcinoma | colon |
| CCL-233 | SW1116 | colorectal adenocarcinoma | colon |
| CCL-237 | SW948 | colorectal adenocarcinoma | colon |
| CCL-238 | SW1417 | colorectal adenocarcinoma | colon |
| CCL-255 | LS123 | colorectal adenocarcinoma | colon |
| CL-187 | LS 180 | colorectal adenocarcinoma | colon |
| CL-188 | LS 174T | colorectal adenocarcinoma | colon |
| CRL-2102 | C2BBe1 | colorectal adenocarcinoma | colon |
| CRL-7214 | Hs 257.T | colorectal adenocarcinoma | colon |
| CRL-7351 | Hs 586.T | colorectal adenocarcinoma | colon |
| CRL-7352 | Hs 587.Int | colorectal adenocarcinoma | colon |
| HTB-37 | Caco-2 | colorectal adenocarcinoma | colon |
| HTB-38 | HT-29 | colorectal adenocarcinoma | colon |
| HTB-39 | SK-CO-1 | colorectal adenocarcinoma | colon |
| CCL-234 | SW1463 | colorectal adenocarcinoma | rectum |
| CRL-7159 | Hs 200.T | colorectal adenocarcinoma | rectum |
| CRL-7184 | Hs 219.T | colorectal adenocarcinoma | rectum |
| CRL-7168 | Hs 207.T | colorectal adenocarcinoma | sigmoid colon |
| CCL-250 | SNU-C2B | colorectal carcinoma | cecum |
| CCL-250.1 | SNU-C2A | colorectal carcinoma | cecum |
| CRL-2134 | LS513 | colorectal carcinoma | cecum |
| CRL-2158 | LS1034 | colorectal carcinoma | cecum |
| CRL-2159 | LS411N | colorectal carcinoma | cecum |
| CCL-247 | HCT 116 | colorectal carcinoma | colon |
| CCL-248 | T84 | colorectal carcinoma | colon |
| CRL-7399 | Hs 674.T/cc | colorectal carcinoma | rectum |
| CRL-7456 | Hs 722.T | colorectal carcinoma | rectum |
| CRL-7273 | Hs 398.T | condyloma acuminatum | skin; genital wart |
| CRL-2105 | HH | cutaneous T cell lymphoma | peripheral blood; T lymphocyte |
| CRL-8294 | MJ | cutaneous T cell lymphoma; mycosis fungoides | peripheral blood; T lymphocyte |
| CRL-7252 | Hs 357.T | dermatofibrosarcoma | skin |
| CRL-7692 | Hs 941.T | dermatofibrosarcoma | skin |
| CRL-7043 | Hs 63.T | dermatofibrosarcoma protuberans | skin |
| CRL-7233 | Hs 295.T | dermatofibrosarcoma protuberans | skin |

TABLE 1-continued

Exemplary Tumor Cell Lines

| ATCC No. | Name | Cancer Type | Tissue Source |
|---|---|---|---|
| HTB-186 | Daoy | desmoplastic cerebellar medulloblastoma | brain; cerebellum |
| CRL-2260 | HT | diffuse mixed lymphoma | ascites; B lymphoblast |
| CRL-2558 | PL45 | ductal adenocarcinoma | pancreas |
| CRL-1918 | CFPAC-1 | ductal adenocarcinoma; | pancreas |
| CRL-12420 | GI-101A | ductal adenocarcinoma; infiltrating | mammary gland; breast; duct |
| CRL-1500 | ZR-75-1 | ductal carcinoma | mammary gland; breast; ascites; epithelial |
| CRL-1504 | ZR-75-30 | ductal carcinoma | mammary gland; breast; ascites; epithelial |
| CRL-1897 | UACC-812 | ductal carcinoma | mammary gland; breast |
| CRL-2320 | HCC1008 | ductal carcinoma | mammary gland; breast |
| CRL-2338 | HCC1954 | ductal carcinoma | mammary gland; breast; duct |
| CRL-7345 | Hs 574.T | ductal carcinoma | mammary gland; breast; duct |
| HTB-121 | BT-483 | ductal carcinoma | mammary gland; breast |
| HTB-129 | MDA-MB-435S | ductal carcinoma | mammary gland; breast; pleural effusion |
| HTB-133 | T-47D | ductal carcinoma | mammary gland; breast; pleural effusion |
| HTB-20 | BT-474 | ductal carcinoma | mammary gland; breast |
| HTB-25 | MDA-MB-175 | ductal carcinoma | mammary gland; breast; pleural effusion |
| CRL-1837 | SU.86.86 | ductal carcinoma | pancreas |
| HTB-104 | Cates-1B | embryonal carcinoma | testis |
| CRL-7802 | Hs 454.T | eosinophilic granuloma | bone |
| CRL-1550 | Ca Ski | epidermoid carcinoma | cervix |
| CRL-7932 | ME180 | epidermoid carcinoma | cervix |
| HTB-33 | ME-180 | epidermoid carcinoma | cervix |
| HTB-34 | MS751 | epidermoid carcinoma | cervix |
| CRL-1555 | A-431 | epidermoid carcinoma | epidermis |
| CRL-7902 | A253 | epidermoid carcinoma | epidermis |
| CCL-199 | HLF-a | epidermoid carcinoma | lung |
| HTB-54 | Calu-1 | epidermoid carcinoma | lung |
| CRL-7228 | Hs 284.Pe | epidermoid carcinoma | lung; pleural effusion |
| CRL-7905 | A388 | epidermoid carcinoma | metastasis to lymph node |
| CRL-2592 | A431NS | epidermoid carcinoma | skin, epidermis |
| HTB-41 | A-253 | epidermoid carcinoma | submaxillary salivary gland |
| CRL-1469 | PANC-1 | epithelioid carcinoma | pancreas; duct |
| CRL-2138 | VA-ES-BJ | epithelioid carcinoma | metastasis to bone marrow |
| CRL-7556 | Hs 822.T | Ewing's sarcoma | bone |
| CRL-7598 | Hs 863.T | Ewing's sarcoma | bone |
| HTB-166 | RD-ES | Ewing's sarcoma | bone |
| CRL-7744 | TE 115.T | fibromatosis | connective and soft tissue |
| CRL-7951 | HT 1080.T | fibrosarcoma | bone |
| CRL-7062 | Hs 93.T | fibrosarcoma | connective and soft tissue |
| CRL-7287 | Hs 414.T | fibrosarcoma | connective tissue |
| CRL-7508 | Hs 778(A).T | fibrosarcoma | connective tissue |
| CRL-7509 | Hs 778(B).T | fibrosarcoma | connective tissue |
| CRL-7664 | Hs 913(B).T | fibrosarcoma | connective tissue |
| CRL-7665 | Hs 913(C).T | fibrosarcoma | connective tissue |
| CRL-7824 | Hs 15.T | fibrosarcoma | connective tissue |
| HTB-152 | Hs 913T | fibrosarcoma | metastasis to lung |
| CRL-7666 | Hs 913(D).T | fibrosarcoma | metastasis to lung or bronchus |
| CRL-7668 | Hs 913(F).T | fibrosarcoma | metastasis to lung or bronchus |
| CCL-121 | HT-1080 | fibrosarcoma | unknown |
| CRL-7604 | Hs 868.T | fibrosarcoma | unknown |
| HTB-91 | SW 684 | fibrosarcoma | unknown |
| TIB-223 | GCT | fibrous histiocytoma | metastasis to lung |
| CRL-7773 | TE 615.T | ganglioneuroblastoma | brain |
| CRL-1739 | AGS | gastric adenocarcinoma | stomach |
| CRL-1863 | RF-48 | gastric adenocarcinoma | stomach |
| CRL-1864 | RF-1 | gastric adenocarcinoma | stomach |
| CRL-5822 | NCI-N87 | gastric carcinoma | stomach |
| HTB-135 | Hs 746T | gastric carcinoma | stomach |
| CRL-5971 | NCI-SNU-1 | gastric carcinoma | stomach; ascites |
| CRL-5973 | NCI-SNU-5 | gastric carcinoma | stomach; ascites |
| CRL-5974 | NCI-SNU-16 | gastric carcinoma | stomach; ascites |
| HTB-103 | KATO III | gastric carcinoma | stomach; pleural effusion |
| CRL-7447 | Hs 706.T | giant cell sarcoma | bone |
| CRL-7473 | Hs 737.T | giant cell sarcoma | bone |
| CRL-7554 | Hs 821.T | giant cell sarcoma | bone |
| CRL-7579 | Hs 846.T | giant cell sarcoma | bone |
| CRL-7617 | Hs 883.T | giant cell sarcoma | bone |
| CRL-7081 | Hs 127.T | giant cell sarcoma | connective tissue |

TABLE 1-continued

Exemplary Tumor Cell Lines

| ATCC No. | Name | Cancer Type | Tissue Source |
|---|---|---|---|
| CRL-7547 | Hs 814.T | giant cell sarcoma | vertebral column |
| CRL-1620 | A172 | glioblastoma | brain |
| CRL-2020 | DBTRG-05MG | glioblastoma | brain; glial cell |
| CRL-7899 | A172 | glioblastoma | brain; glial cell |
| HTB-16 | U-138 MG | glioblastoma | brain |
| CRL-1690 | T98G | glioblastoma multiforme | brain |
| HTB-14 | U-87 MG | glioblastoma; astrocytoma | brain |
| HTB-15 | U-118 MG | glioblastoma; astrocytoma | brain |
| HTB-138 | Hs 683 | glioma | brain |
| CRL-10741 | C3A | hepatoblastoma | liver |
| CRL-11997 | HEP G2/2.2.1 | hepatoblastoma; transfected with a CYP7 minigene/luciferase construct | liver |
| CRL-2233 | SNU-398 | hepatocellular carcinoma | liver |
| CRL-2234 | SNU-449 | hepatocellular carcinoma | liver |
| CRL-2235 | SNU-182 | hepatocellular carcinoma | liver |
| CRL-2236 | SNU-475 | hepatocellular carcinoma | liver |
| HB-8064 | Hep 3B2.1-7 (Hep 3B) | hepatocellular carcinoma | liver |
| HB-8065 | Hep G2 | hepatocellular carcinoma | liver |
| CRL-8024 | PLC/PRF/5 | hepatoma | liver; Alexander cells |
| CRL-1532 | 182-PF SK | hereditary adenomatosis | skin |
| CRL-1533 | 166-ME SK | hereditary adenomatosis (Gardner's variant) | skin |
| CRL-1593.2 | U-937 | histiocytic lymphoma | macrophage; histiocyte |
| CRL-2367 | TUR | histiocytic lymphoma; transfected U-937 cells | histiocyte |
| CRL-7593 | Hs 856.T | histiocytoma | connective tissue |
| CCL-113 | RPMI 6666 | Hodgkin's disease; Hodgkin's lymphoma | unknown |
| CRL-7264 | Hs 388.T | Hodgkin's disease; Hodgkin's lymphoma | lymph node |
| CRL-7362 | Hs 604.T | Hodgkin's disease; Hodgkin's lymphoma | lymph node |
| CRL-7488 | Hs 751.T | Hodgkin's disease; Hodgkin's lymphoma | lymph node |
| HTB-146 | Hs 445 | Hodgkin's disease; Hodgkin's lymphoma | lymph node |
| CRL-7779 | TO 175.T | Hodgkin's disease; Hodgkin's lymphoma | skin |
| CRL-7373 | Hs 611.T | Hodgkin's disease; Hodgkin's lymphoma | spleen |
| CRL-7378 | Hs 616.T | Hodgkin's disease; Hodgkin's lymphoma | thymus |
| CRL-2175 | SW 156 | hypernephroma | kidney |
| CCL-244 | HCT-8 (HRT-18) | ileocecal colorectal adenocarcinoma | colon |
| CRL-7428 | Hs 692(A).T | intestinal carcinoma | metastasis to lymph node |
| CRL-7630 | Hs 892.T | keratoacanthoma | skin |
| CRL-7629 | Hs 891.T | kidney carcinoma | metastasis to lymph node |
| CRL-5878 | NCI-H1581 | large cell adenocarcinoma | lung |
| CRL-2262 | 29SR | large cell immunoblastic lymphoma | pleural effusion; lymphoblast |
| CRL-2289 | DB | large cell lymphoma | B lymphoblast |
| CRL-5923 | NCI-H2106 | large cell neuroendocrine carcinoma | lung metastasis to lymph node |
| CRL-7822 | Hs 5.T | leiomyosarcoma | connective tissue |
| HTB-88 | SK-LMS-1 | leiomyosarcoma | vulva |
| CRL-10423 | JM1 | leukemia; lymphoma | pre-B lymphoblast |
| HTB-92 | SW 872 | liposarcoma | unknown |
| CRL-7306 | Hs 505.T | lymphocytic lymphoma | lymph node |
| CRL-7313 | Hs 518.T | lymphocytic lymphoma | spleen |
| CRL-7818 | Hs 491.T | lymphocytic lymphoma | lymph node |
| CRL-7218 | Hs 268.T | lymphogranulomatosis | lymph node |
| CRL-2230 | BC-1 | lymphoma | B lymphocyte |
| CRL-2231 | BC-2 | lymphoma | B lymphocyte |
| CRL-2277 | BC-3 | lymphoma | B lymphocyte |
| CRL-8119 | 1A2 | lymphoma | B lymphocyte |
| HTB-142 | Hs 602 | lymphoma | cervical lymph node |
| CRL-11622 | RH9/CB | lymphoma | cutaneous T lymphocyte |
| CRL-12043 | RH9 | lymphoma | cutaneous T lymphocyte |
| HTB-176 | H9 | lymphoma | cutaneous T lymphocyte |
| TIB-161 | HuT 78 | lymphoma | cutaneous T lymphocyte |
| CRL-7235 | Hs 313.T | lymphoma | lymph node |
| CRL-7507 | Hs 777.T | lymphoma | lymph node |

TABLE 1-continued

Exemplary Tumor Cell Lines

| ATCC No. | Name | Cancer Type | Tissue Source |
|---|---|---|---|
| CRL-11213 | RH9/MSC | lymphoma | T lymphocyte |
| CRL-8543 | H9/HTLV-IIIB | lymphoma | T lymphocyte |
| CRL-7797 | HT 1417 | lymphoma | unknown |
| TIB-162 | HuT 102 | lymphoma; mycosis fungoides | cutaneous T lymphocyte |
| CRL-7755 | TE 175.T | lymphosarcoma | lymph node |
| CRL-7641 | Hs 898.T | malignant acanthocytosis; keratoacanthoma | skin |
| HTB-105 | Tera-1 | malignant embryonal carcinoma | embryo |
| HTB-106 | Tera-2 | malignant embryonal carcinoma | embryo |
| CRL-2365 | M059K | malignant glioblastoma; glioma | brain; glial cell |
| CRL-2366 | M059J | malignant glioblastoma; glioma | brain; glial cell |
| CRL-7684 | Hs 934.T | malignant melanoma | connective tissue |
| CRL-7685 | Hs 935.T | malignant melanoma | connective tissue |
| HTB-64 | Malme-3M | malignant melanoma | metastasis to lung |
| HTB-63 | HT-144 | malignant melanoma | metastasis to subcutaneous tissue |
| CRL-1424 | G-361 | malignant melanoma | skin |
| CRL-1619 | A-375 | malignant melanoma | skin |
| CRL-1872 | A375.S2 | malignant melanoma | skin |
| CRL-1974 | COLO 829 | malignant melanoma | skin |
| CRL-7691 | Hs 940.T | malignant melanoma | skin |
| HTB-65 | MeWo | malignant melanoma | skin |
| HTB-66 | RPMI-7951 | malignant melanoma | skin |
| HTB-67 | SK-MEL-1 | malignant melanoma | skin |
| HTB-68 | SK-MEL-2 | malignant melanoma | skin |
| HTB-69 | SK-MEL-3 | malignant melanoma | skin |
| HTB-70 | SK-MEL-5 | malignant melanoma | skin |
| HTB-71 | SK-MEL-24 | malignant melanoma | skin |
| HTB-72 | SK-MEL-28 | malignant melanoma | skin |
| HTB-73 | SK-MEL-31 | malignant melanoma | skin |
| CRL-2407 | NK-92 | malignant non-Hodgkin's lymphoma | natural killer cell; NK cell |
| CRL-11732 | OV-90 | malignant papillary serous adenocarcinoma | ovary |
| CRL-1973 | NTERA-2 cl.D1 | malignant pluripotent embryonal carcinoma | testis |
| CRL-8805 | TE671 | medulloblastoma | brain; cerebellum |
| HTB-185 | D283 Med | medulloblastoma | brain; cerebellum |
| HTB-187 | D341 Med | medulloblastoma | brain; cerebellum |
| CRL-7724 | SH-4 | melanoma | lung, pleural effusion |
| CRL-7426 | Hs 688(B).T | melanoma | metastasis to lymph node |
| CRL-7568 | Hs 834.T | melanoma | metastasis to lymph node |
| CRL-11147 | A2058 | melanoma | skin |
| CRL-1675 | WM-115 | melanoma | skin |
| CRL-1676 | WM-266-4 | melanoma | skin |
| CRL-2500 | A7 | melanoma | skin |
| CRL-7299 | Hs 432.T | melanoma | skin |
| CRL-7360 | Hs 600.T | melanoma | skin |
| CRL-7425 | Hs 688(A).T | melanoma | skin |
| CRL-7572 | Hs 839.T | melanoma | skin |
| CRL-7585 | Hs 852.T | melanoma | skin |
| CRL-7637 | Hs 895.T | melanoma | skin |
| CRL-7653 | Hs 906(A).T | melanoma | skin |
| CRL-7654 | Hs 906(B).T | melanoma | skin |
| CRL-7658 | Hs 908.Sk | melanoma | skin |
| CRL-7686 | Hs 936.T | melanoma | skin |
| CRL-7687 | Hs 936.T(C1) | melanoma | skin |
| CRL-7690 | Hs 939.T | melanoma | skin |
| CRL-7898 | A101D | melanoma | skin |
| CRL-7904 | A375 | melanoma | skin |
| CRL-9446 | CHL-1 | melanoma | skin |
| CRL-9451 | CHL-2 | melanoma | skin |
| CRL-9607 | HMCB | melanoma | skin |
| HTB-140 | Hs 294T | melanoma | skin |
| HTB-114 | SK-UT-1 | mesodermal tumor (mixed) consistent with leiomyosarcoma | uterus |
| HTB-115 | SK-UT-1B | mesodermal tumor (mixed); consistent with leiomyosarcoma | uterus; endometrium |
| CRL-5820 | NCI-H28 | mesothelioma | pleural effusion |
| CRL-5915 | NCI-H2052 | mesothelioma | pleural effusion |

TABLE 1-continued

Exemplary Tumor Cell Lines

| ATCC No. | Name | Cancer Type | Tissue Source |
|---|---|---|---|
| CRL-5917 | NCI-H2066 | mixed; small cell lung cancer; adenocarcinoma; squamous cell carcinoma | lung |
| CRL-5938 | NCI-H2286 | mixed; small cell lung cancer; adenocarcinoma; squamous cell carcinoma | lung |
| CRL-1848 | NCI-H292 | mucoepidermoid pulmonary carcinoma | lung |
| CRL-8644 | HuNS1 | myeloma | lymphoblast |
| CCL-127 | IMR-32 | neuroblastoma | brain; neuroblast |
| CRL-2137 | SK-N-AS | neuroblastoma | brain; neuroblast |
| CRL-2142 | SK-N-FI | neuroblastoma | brain; neuroblast |
| CRL-2149 | SK-N-DZ | neuroblastoma | brain; neuroblast |
| CRL-2266 | SH-SY5Y | neuroblastoma | brain |
| CRL-2267 | BE(2)-M17 | neuroblastoma | brain |
| CRL-2268 | BE(2)-C | neuroblastoma | brain |
| CRL-2270 | MC-IXC | neuroblastoma | brain |
| CRL-2271 | SK-N-BE(2) | neuroblastoma | brain |
| CRL-2273 | CHP-212 | neuroblastoma | brain |
| HTB-11 | SK-N-SH | neuroblastoma | brain |
| CRL-5893 | NCI-H1770 | neuroendocrine carcinoma | lymph node |
| HTB-10 | SK-N-MC | neuroepithelioma | brain |
| HTB-148 | H4 | neuroglioma | brain |
| CRL-7434 | Hs 697.Ln | non-caseating granuloma | lymph node |
| CRL-10236 | 10C9 | non-Hodgkin's lymphoma | lymph node; B lymphocyte |
| CRL-2261 | RL | non-Hodgkin's lymphoma | ascites; B lymphoblast |
| CRL-2408 | NK-92MI | non-Hodgkin's lymphoma, malignant; transfected with human IL-2 cDNA | lymphoblast |
| CRL-2073 | NCCIT | nullipotent embryonal carcinoma; teratocarcinoma | bone |
| CRL-7609 | Hs 871.T | osteoblastoma | bone |
| CRL-11226 | 143.98.2 | osteosarcoma | bone |
| CRL-1423 | G-292 | osteosarcoma | bone |
| CRL-1427 | MG-63 | osteosarcoma | bone |
| CRL-1543 | HOS | osteosarcoma | bone |
| CRL-1544 | KHOS/NP | osteosarcoma | bone |
| CRL-1545 | KHOS-240S | osteosarcoma | bone |
| CRL-1546 | KHOS-321H | osteosarcoma | bone |
| CRL-1547 | MNNG/HOS | osteosarcoma | bone |
| CRL-7005 | Hs 3.T | osteosarcoma | bone |
| CRL-7023 | Hs 39.T | osteosarcoma | bone |
| CRL-7060 | Hs 88.T | osteosarcoma | bone; connective tissue |
| CRL-7134 | Hs 184.T | osteosarcoma | bone |
| CRL-7140 | Hs 188.T | osteosarcoma | bone |
| CRL-7263 | Hs 387.T | osteosarcoma | bone |
| CRL-7444 | Hs 704.T | osteosarcoma | bone |
| CRL-7448 | Hs 707(A).T | osteosarcoma | bone |
| CRL-7471 | Hs 735.T | osteosarcoma | bone |
| CRL-7489 | Hs 755(B).T | osteosarcoma | bone |
| CRL-7511 | Hs 781.T | osteosarcoma | bone |
| CRL-7521 | Hs 792(B).T | osteosarcoma | bone |
| CRL-7537 | Hs 805.T | osteosarcoma | bone |
| CRL-7543 | Hs 811.T | osteosarcoma | bone |
| CRL-7577 | Hs 845.T | osteosarcoma | bone |
| CRL-7595 | Hs 860.T | osteosarcoma | bone |
| CRL-7600 | Hs 864.T | osteosarcoma | bone; connective tissue |
| CRL-7602 | Hs 866.T | osteosarcoma | bone |
| CRL-7606 | Hs 870.T | osteosarcoma | bone |
| CRL-7622 | Hs 888.T | osteosarcoma | bone |
| CRL-7626 | Hs 889.T | osteosarcoma | bone |
| CRL-7628 | Hs 890.T | osteosarcoma | bone |
| CRL-7631 | Hs 894(A).T | osteosarcoma | bone |
| CRL-7632 | Hs 894(B).T | osteosarcoma | bone |
| CRL-7633 | Hs 894(C).T | osteosarcoma | bone |
| CRL-7634 | Hs 894(D).T | osteosarcoma | bone |
| CRL-7642 | Hs 899(A).T | osteosarcoma | bone |
| CRL-7643 | Hs 899(B).T | osteosarcoma | bone |
| CRL-7644 | Hs 899(C).T | osteosarcoma | bone |
| CRL-7645 | Hs 899(D) | osteosarcoma | bone |
| CRL-7765 | TE 417.T | osteosarcoma | bone |
| CRL-7766 | TE 418.T | osteosarcoma | bone |
| CRL-7780 | TO 203.T | osteosarcoma | bone |
| CRL-7783 | HT 728.T | osteosarcoma | bone |
| CRL-7823 | Hs 14.T | osteosarcoma | bone |

TABLE 1-continued

Exemplary Tumor Cell Lines

| ATCC No. | Name | Cancer Type | Tissue Source |
|---|---|---|---|
| CRL-7939 | SaOS | osteosarcoma | bone |
| CRL-7943 | T1-73 | osteosarcoma | bone |
| CRL-8303 | 143B | osteosarcoma | bone |
| CRL-8304 | 143B | osteosarcoma | bone |
| HTB-85 | Saos-2 | osteosarcoma | bone |
| HTB-96 | U-2 OS | osteosarcoma | bone |
| CRL-2098 | SJSA-1 | osteosarcoma | bone |
| CRL-7677 | Hs 925.T | pagetoid sarcoma | skin |
| CRL-5819 | NCI-H1404 | papillary adenocarcinoma | lung |
| CRL-7573 | Hs 840.T | papilloma | pharynx |
| CCL-155 | RPMI 8226 | plasmacytoma; myeloma | B lymphocyte |
| CRL-8033-1 | SKO-007 | plasmacytoma; myeloma | B lymphocyte |
| CRL-8033-2 | SKO-007 | plasmacytoma; myeloma | B lymphocyte |
| CRL-8083 | MC/CAR | plasmacytoma; myeloma | B lymphocyte |
| CRL-8147 | MC/CAR-Z2 | plasmacytoma; myeloma | B lymphocyte |
| TIB-196 | U266B1 | plasmacytoma; myeloma | B lymphocyte |
| CRL-9068 | NCI-H929 | plasmacytoma; myeloma | bone marrow; B lymphocyte |
| CRL-2237 | SNU-387 | pleomorphic hepatocellular carcinoma | liver |
| CRL-2238 | SNU-423 | pleomorphic hepatocellular carcinoma | liver |
| CRL-5904 | NCI-H1915 | poorly differentiated carcinoma | brain |
| CRL-7753 | TE 161.T | possible Burkitt's lymphoma | lymph node |
| CRL-2335 | HCC1806 | primary acantholytic squamous cell carcinoma | mammary gland; breast |
| CRL-1902 | UACC-893 | primary ductal carcinoma | mammary gland; breast |
| CRL-2314 | HCC38 | primary ductal carcinoma | mammary gland; breast; duct |
| CRL-2315 | HCC70 | primary ductal carcinoma | mammary gland; breast; duct |
| CRL-2316 | HCC202 | primary ductal carcinoma | mammary gland; breast; duct |
| CRL-2321 | HCC1143 | primary ductal carcinoma | mammary gland; breast; duct |
| CRL-2322 | HCC1187 | primary ductal carcinoma | mammary gland; breast; duct |
| CRL-2324 | HCC1395 | primary ductal carcinoma | mammary gland; breast |
| CRL-2326 | HCC1419 | primary ductal carcinoma | mammary gland; breast |
| CRL-2329 | HCC1500 | primary ductal carcinoma | mammary gland; breast; duct |
| CRL-2331 | HCC1599 | primary ductal carcinoma | mammary gland; breast; duct |
| CRL-2336 | HCC1937 | primary ductal carcinoma | mammary gland; breast; duct |
| CRL-2340 | HCC2157 | primary ductal carcinoma | mammary gland; breast |
| CRL-2343 | HCC2218 | primary ductal carcinoma | mammary gland; breast; duct |
| CRL-11730 | TOV-21G | primary malignant adenocarcinoma | ovary |
| CRL-11731 | TOV-112D | primary malignant adenocarcinoma | ovary |
| CRL-2380 | MPanc-96 | primary malignant adenocarcinoma | pancreas |
| CRL-2330 | HCC1569 | primary metaplastic carcinoma | mammary gland; breast |
| CCL-105 | SW-13 | primary small cell carcinoma | adrenal gland; cortex |
| CRL-1231 | Sar Nis | pseudoachondroplasia (autosomal dominant) | skin |
| CRL-1611 | ACHN | renal cell adenocarcinoma | kidney |
| CRL-1932 | 786-O | renal celladenocarcinoma | kidney |
| CRL-1933 | 769-P | renal celladenocarcinoma | kidney |
| CRL-1440 | G-402 | renal leiomyoblastoma | kidney |
| CRL-7678 | Hs 926.T | renal rhabdomyosarcoma | kidney |
| CRL-7239 | Hs 324.T | reticulum cell sarcoma | lymph node |
| HTB-169 | WERI-Rb-1 | retinoblastoma | eye; retina |
| HTB-18 | Y79 | retinoblastoma | eye; retina |
| CRL-7713 | 130T | rhabdomyosarcoma | connective and soft tissue |
| CRL-7726 | T 174 | rhabdomyosarcoma | connective and soft tissue |
| CRL-7763 | TE 381.T | rhabdomyosarcoma | connective and soft tissue |
| CRL-7767 | TE 441.T | rhabdomyosarcoma | connective tissue |
| CRL-7774 | TE 617.T | rhabdomyosarcoma | connective tissue |
| CRL-7862 | Hs 729.T | rhabdomyosarcoma | connective tissue |
| CCL-136 | RD | rhabdomyosarcoma | muscle |
| CRL-1598 | A-673 | rhabdomyosarcoma | muscle |
| CRL-2061 | SJRH30 | rhabdomyosarcoma | muscle |
| CRL-7752 | TE 159.T | rhabdomyosarcoma | unknown |
| CRL-7900 | A204 | rhabdomyosarcoma | unknown |
| HTB-153 | Hs 729 | rhabdomyosarcoma | unknown |
| HTB-82 | A-204 | rhabdomyosarcoma | unknown |
| CRL-7910 | A673 | rhabdomyosarcoma or undifferentiated carcinoma | unknown |
| CRL-7732 | TE 76.T | sacrococcygeal teratoma | bone |
| CRL-7746 | TE 130.T | sacrococcygeal teratoma | bone |

TABLE 1-continued

Exemplary Tumor Cell Lines

| ATCC No. | Name | Cancer Type | Tissue Source |
|---|---|---|---|
| HTB-86 | SK-ES-1 | sarcoma (anaplastic osteosarcoma or Ewing's sarcoma) | bone |
| CRL-7037 | Hs 57.T | sarcoma or lymphoma | lung |
| CRL-7482 | Hs 742.T | scirrhous adenocarcinoma | mammary gland; breast |
| CRL-7800 | Hs 444(B).T | seminoma | testis |
| CRL-7030 | Hs 51.T | spindle cell sarcoma | connective and soft tissue |
| CRL-7085 | Hs 132.T | spindle cell sarcoma | connective tissue |
| CRL-10302 | SW756 | squamous cell carcinoma | cervix |
| HTB-35 | SiHa | squamous cell carcinoma | cervix |
| CRL-5928 | NCI-H2170 | squamous cell carcinoma | lung |
| HTB-182 | NCI-H520 | squamous cell carcinoma | lung |
| HTB-59 | SW 900 | squamous cell carcinoma | lung |
| HTB-58 | SK-MES-1 | squamous cell carcinoma | lung; pleural effusion |
| CCL-30 | RPMI 2650 | squamous cell carcinoma | nasal septum; pleural effusion |
| HTB-43 | FaDu | squamous cell carcinoma | pharynx |
| HTB-107 | SW579 | squamous cell carcinoma | thyroid |
| CRL-1623 | SCC-15 | squamous cell carcinoma | tongue |
| CRL-1624 | SCC-4 | squamous cell carcinoma | tongue |
| CRL-1628 | SCC-25 | squamous cell carcinoma | tongue |
| CRL-1629 | SCC-9 | squamous cell carcinoma | tongue |
| CRL-2095 | CAL 27 | squamous cell carcinoma | tongue |
| HTB-3 | SCaBER | squamous cell carcinoma | urinary bladder |
| HTB-117 | SW 954 | squamous cell carcinoma | vulva |
| CRL-5826 | NCI-H226 | squamous cell carcinoma; mesothelioma | lung; pleural effusion |
| CRL-7289 | Hs 416.T | squamous papilloma | skin |
| CRL-7440 | Hs 701.T | synovial sarcoma | connective tissue |
| HTB-93 | SW 982 | synovial sarcoma | synovium |
| CRL-1572 | PA-1 | teratocarcinoma | ovary |
| CRL-7886 | Hs 789.T | transitional cell carcinoma | ureter |
| CRL-7882 | Hs 769.T | transitional cell carcinoma | urethra |
| CRL-1749 | UM-UC-3 | transitional cell carcinoma | urinary bladder |
| CRL-2169 | SW 780 | transitional cell carcinoma | urinary bladder |
| HTB-1 | J82 | transitional cell carcinoma | urinary bladder |
| HTB-4 | T24 | transitional cell carcinoma | urinary bladder |
| HTB-5 | TCCSUP | transitional cell carcinoma | urinary bladder |
| HTB-2 | RT4 | transitional cell papilloma | urinary bladder |
| CRL-1649 | MC116 | undifferentiated lymphoma | ascites; B lymphocyte |
| CRL-1976 | MES-SA | uterine sarcoma | uterus |
| CRL-2274 | MES-SA/MX2 | uterine sarcoma | uterus |
| CRL-1977 | MES-SA/Dx5 | uterine sarcoma; multiple drug resistant | uterus |
| CRL-7102 | Hs 156.T | xanthogranuloma | skin |

The tumor can but need not necessarily be a tumor of human origin. In one embodiment the tumor is a Lewis lung model.

As used herein, implanting refers to a surgical procedure of placing an intact or nondispersed tumor or other composition in the body of a vertebrate. Implantation can be carried out at any suitable site in the body of the host vertebrate. In one embodiment implantation is subcutaneous, i.e., between the skin and muscle of the vertebrate. In one embodiment implantation is intraperitoneal. Other sites of implantation are contemplated by the invention and specifically include any site toward which it is desired to direct tissue regeneration. The spatial direction of tissue generation is influenced by a gradient of tumor products emanating from the implant.

As used herein, an intact tumor refers to a population of tumor cells having a three-dimensional architecture including extracellular matrix and/or stromal structures generated by the tumor cells as developed when the tumor cells are grown in vivo or in vitro. Intact tumor is to be distinguished from dispersed tumor, the latter referring to any preparation of tumor cells in which the three-dimensional architecture of the intact tumor has been substantially eliminated, e.g., to create a single-cell suspension of tumor cells.

As used herein, a nondispersed portion of an intact tumor refers to a section of an intact tumor having the three-dimensional architecture of the tumor from which the portion is derived. A nondispersed portion of an intact tumor is to be distinguished from a dispersed portion of a tumor, the latter referring to any preparation of tumor cells in which the three-dimensional architecture of a portion of an intact tumor has been substantially eliminated, e.g., to create a single-cell suspension of tumor cells. In one embodiment the nondispersed portion of an intact tumor refers to a segment of intact tumor that has been dissected from the intact tumor. The dissecting in one embodiment involves cutting by any suitable means, e.g., scalpel or scissors. In one embodiment a nondispersed portion of an intact tumor refers to a portion of an intact tumor that is isolated from a region of intact tumor that excludes both outer cortical tissue and central necrotic tissue.

The tumor implant can be a xenograft, an allograft, or an autograft. As used herein the term xenograft refers to a tissue or organ, for example a tumor or a nondispersed piece of a tumor, from a donor of one species, placed into a recipient of another species. As used herein the term allograft refers to a tissue or organ, for example a tumor or a nondispersed piece of a tumor, from an individual donor of one species, placed into another individual recipient of the same species. As used herein the term autograft refers to a tissue or organ, for example a tumor or a nondispersed piece of a tumor, from an individual as donor, placed into the same individual as recipient. Xenografts and allografts may be rejected by an intact immune system of the recipient. Thus in some embodiments the recipient is chosen or manipulated to have an incompetent immune system. In one embodiment the recipient is a SCID mouse.

As used herein, a vertebrate refers to any vertebrate animal, including mammals, fish, birds, reptiles, and amphibians. In one embodiment the vertebrate is a mammal. In one embodiment the mammal is a non-primate mammal, for example, a mouse, rat, rabbit, guinea pig, sheep, pig, goat, or dog. In one embodiment the mammal is a mouse. In one embodiment the mammal is a non-human primate. In one embodiment the mammal is a human. In one embodiment the vertebrate is a fish, e.g., a zebrafish.

Various aspects of the invention include the step of growing the implanted tumor or portion thereof in a vertebrate for at least a selected time. As used herein, growing refers to permitting the implanted tumor or portion thereof to reside in a viable state within the vertebrate host. In one embodiment growing involves an increase in tumor cell population. In one embodiment growing involves an increase in tumor size (e.g., volume). For example, in a typical situation a tumor implant may be 1 mm$^3$ at the time of implantation and at least 1 cm$^3$ after the selected time, a 1000-fold increase in size.

The selected time is any time sufficient to permit establishment of a vasculogenic program and, optionally, at least a desired size. The selected time can range from one day up to one year. In one embodiment at least a selected time is a selected time ranging from one day up to one year. In certain various embodiments the selected time is one day, two days, three days, four days, five days, six days, one week, two weeks, three weeks, four weeks, two months, three months, four months, five months, and six months. In a typical situation the selected time is about one month.

In certain embodiments the implanting and growing steps are repeated serially. A further step of selecting a tumor based on its vasculogenic program, increased vasculogenic program, or reduced angiogenic program, is optionally included after the preceding step of growing, thereby selecting for tumors with the desired phenotype. Each subsequent round of implanting and growing steps are typically performed in a naive vertebrate host, i.e., tumor implanted and grown in host n in round n is implanted and grown in host n+1 in round n+1. Thus a tumor or portion thereof is allowed to grow in a first vertebrate host for the selected amount of time, evaluated for its vasculogenic program, and then used as the tumor or portion thereof implanted into and grown in a second or subsequent vertebrate host. In one embodiment the steps of implanting and growing are performed twice. In one embodiment the steps of implanting and growing are performed three times. In one embodiment the steps of implanting and growing are performed four times. In various embodiments the steps of implanting and growing are performed 5, 6, 7, 8, 9, 10, 11, 12, 13, 14, 15, 16, 17, 18, 19, or 20 times.

The invention in certain aspects relates to a method for isolating a selected type of living tissue from a tumor. As used herein, a selected type of tissue can be any type of tissue generated or induced by the tumor. In one embodiment the selected type of tissue is an artery. In one embodiment the selected type of tissue is a vein. In one embodiment the selected type of tissue is nerve. In one embodiment the selected type of tissue is a specific type of cell, particularly a stem cell. The selected type of tissue can be isolated from the tumor and then used for any suitable purpose, including a therapeutic purpose.

In one embodiment the isolating can be accomplished in vivo. For example, a neurovascular bundle induced by the tumor can be dissected away from surrounding tissues in a living host, without severing connection between the tumor and the host. The artery and vein of the induced neurovascular bundle may be exposed so that they can be cannulated with a needle or catheter in order to permit sampling of arterial influx to the tumor and venous efflux from the tumor, respectively.

In one embodiment the isolating includes removing the selected tissue from the tumor and from the host. The isolated selected tissue in this embodiment is then available, for example, for use in vivo as a tissue implant at another site in the original host or at any desired site in another host. Alternatively, the isolated selected tissue in this embodiment can be used in vitro for further tissue engineering or characterization, for example in metabolic or pharmacological study.

In one embodiment the isolating includes removing the tumor from the selected tissue, leaving intact the connection between the selected tissue and the host. For example, an artery and a vein included in an induced tissue may be used to create an arteriovenous shunt suitable for use in hemodialysis. In another example, an artery and a vein included in an induced tissue may be used as sites for vascular connection of a kidney allograft.

The invention in certain aspects relates to methods for inducing host tissue regeneration. The methods according to these aspects can employ either tumors or tumor products to induce regeneration of host tissue in a treated vertebrate host.

In various embodiments an intact tumor, a nondispersed portion of an intact tumor, or an effective amount of one or more tumor products is implanted into a vertebrate host in need of host tissue regeneration. In one embodiment the tumor is a tumor characterized by a vasculogenic program, as described herein. As the tumor grows within the host, it induces regeneration of host tissues. Likewise, as the tumor product is released into the host, it induces regeneration of host tissues.

In one embodiment the implanted tumor, nondispersed portion of a tumor, or tumor product is contained within a container bounded at least in part by a semipermeable membrane, the membrane selected to permit transfer of soluble products, such as soluble tumor products, oxygen, nutrients, metabolic waste products, and drugs, between the tumor and the host. The container can be composed completely of semipermeable membrane, or it can be composed partly of impermeable wall and partly of semipermeable membrane. The semipermeable membrane is selected to have a pore size and structure such that transfer of cells cannot occur between the tumor and the host.

In one embodiment the semipermeable membrane is biocompatible, i.e., it does not induce a response by the host. In one embodiment the semipermeable membrane is substantially non-resorbable. In one embodiment the semipermeable membrane is resorbable.

As used herein, a vertebrate host in need of tissue regeneration is a vertebrate having a disease or condition that is characterized by absence or disruption of normal tissue, wherein the absent or disrupted normal tissue may be treated by restoration of normal tissue. The list of diseases and conditions that may benefit from tissue regeneration is extensive and includes, without limitation, cardiovascular disease, coronary insufficiency, myocardial infarction, peripheral vascular disease, peripheral neuropathy, spinal cord injury, stroke, Alzheimer's disease, burns, emphysema, cirrhosis, diabetes mellitus, chronic pancreatitis, amputation.

In one embodiment the vertebrate host has peripheral nerve disease (also termed peripheral neuropathy). Peripheral neuropathy can arise from any of a number of conditions, including ischemia, systemic disease such as diabetes mellitus, infectious disease such as Hansen's disease and Lyme disease, genetic conditions, nerve trauma, and exposure to toxins. Genetically-acquired peripheral neuropathies include Refsum's disease, abetalipoproteinemia, Tangier disease, Krabbe's disease, metachromatic leukodystrophy, Fabry's disease, Dejerine-Sottas syndrome, Charcot-Marie Tooth disease, and others. Exemplary toxic agents which cause neurotoxicities include therapeutic drugs such as antineoplastic agents, various alcohols including ethanol, contaminants in foods, and environmental and industrial pollutants.

In one embodiment the vertebrate host has spinal cord injury. Spinal cord injury includes disruption of spinal cord structure at any location and may result, in certain embodiments, in partial or complete hemiplegia, paraplegia, quadriplegia, and any combination thereof.

In one embodiment the vertebrate host has vascular disease involving an artery. Arterial insufficiency can arise from any of a variety of causes, including atherosclerosis, arteriosclerosis, frostbite, diabetes mellitus, thrombosis, trauma, and vasculitis. The vascular disease is one embodiment can be peripheral vascular disease, e.g., vascular disease of the limbs. The vascular disease in one embodiment involves one or more of the coronary arteries.

In one embodiment the implant is implanted into a site toward which direction the tissue regeneration is desired. Without meaning to be bound to any particular theory or mechanism of action, it is believed that the implanted tumor or tumor products generate a gradient of factors, centered at the location of the implant, along which regeneration of tissue occurs. Thus selection of the location of the implant can be made to best advantage depending on the three-dimensional direction toward which it is desired to regenerate tissue. For example, an implant may be implanted at a site distal to a viable peripheral nerve, which site is in need of peripheral nerve regeneration. As another example, an implant may be positioned at a site distal to adequate coronary flow, which site is at risk of further ischemic injury or insufficiency following completed or threatened myocardial infarction.

As an alternative to implanting a tumor or tumor product, in one aspect of the invention an effective amount of a tumor product is administered to a vertebrate subject in need of tissue regeneration, to induce host tissue regeneration. In one embodiment the tumor product is a tumor product isolated from a tumor characterized by a vasculogenic program, as described herein. The administering may be into a site toward which direction the tissue regeneration is desired.

Various aspects of the invention involve implanting, administering, identifying, or isolating a tumor product. As used herein, a tumor product refers to any composition of tumor origin. Tumor products can include soluble factors and cells originating from the tumor. Thus tumor products do not include regenerated host tissue. In one embodiment the tumor product is a product of a tumor characterized by a vasculogenic program, as described herein. Tumor products include, without limitation, such soluble factors as cytokines, growth factors, morphogens, angiogenesis factors, and anti-angiogenesis factors. A tumor product in one embodiment is a tumor cell. In one embodiment the tumor cell is a stem cell.

As used herein, cytokine refers to any of a number of soluble proteins or glycoproteins that act on immune cells through specific receptors to affect the state of activation and function of the immune cells. Cytokines include interferons, interleukins, tumor necrosis factor, transforming growth factor beta, colony-stimulating factors (CSFs), chemokines, cytokines that stimulate hematopoiesis, as well as others. Interferons specifically include, without limitation, interferon alpha (IFN-α), interferon beta (IFN-β), and interferon gamma (IFN-γ). IFN-α includes a family of about twenty structurally related polypeptides encoded by separate genes. Interleukins specifically include, without limitation, interleukin 1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, and IL-32. Chemokines are a family of cytokines that stimulate leukocyte movement and migration. Chemokines specifically include, without limitation, so-called C, CC, CXC, and $CX_3C$ chemokines, BCA-1, CTACK, CXCL16, ELC, ENA78, eotaxin, fractalkine, GCP-2, Gro-α, Gro-β, Gro-γ, I-309, IP-10, I-TAC, lymphotactin, MCP-1, MCP-2, MCP-3, MCP-4, MDC, MEC, MIG, MIP-1α, MIP-1β, MIP-3α, NAP-2, RANTES, SDF-1, SLC, TARC, and TECK. Colony-stimulating factors specifically include, without limitation, granulocyte colony-stimulating factor (G-CSF), granulocyte-monocyte colony-stimulating factor (GM-CSF), and monocyte colony-stimulating factor (M-CSF). Additional cytokines that stimulate hematopoiesis include stem cell factor (c-Kit ligand), erytrhropoietin, and thrombopoietin.

As used herein, growth factor refers to a naturally occurring soluble protein or glycoprotein that stimulates cell division, differentiation, and proliferation. Growth factors are produced by normal cells during embryonic development, tissue growth, and wound healing. Certain growth factors are also considered to be cytokines. Growth factors include, but are not limited to, epidermal growth factor (EGF), acidic fibroblast growth factor (aFGF), basic fibroblast growth factor (bFGF), erythropoietin (EPO), hematopoietic cell growth factor (HCGF), nerve growth factor (NGF), platelet-derived growth factor (PDGF), stem cell factors, neurotrophins, transforming growth factor (TGF), and VEGF.

As used herein, morphogen refers to a substance that provides spatial information via a concentration gradient during embryonic development. Morphogens are usually diffusible proteins such as Sonic hedgehog.

Sonic hedgehog (Shh) is a key developmental morphogen in vertebrates, and it plays an essential role in the development of neuronal cells and tissues in both the peripheral and central nervous system(Lum, L. et al., *Science* 304, 1755-9 (2004)). In addition, it is central in determining dorsal-ventral polarity of the neural tube (Chiang, C. et al., *Nature* 383, 407-13 (1996); Marti, E. et al., *Nature* 375, 322-325 (1995); Ingham, P. W. et al., A. P., *Genes Devel.* 15, 3059-87 (2001)) and the determination of anterior-posterior patterning of limbs. Shh is but one member of the hedgehog protein family, which also includes Indian (Ihh) and Desert (Dhh). Sonic hedgehog signaling has long been considered to be active only during development. However, there are recent reports of continued Shh activity in adult stem cells (Lai, K. et al., *Nature Neurosci.* 6(1), 21-27 (2003); Ruiz i Altaba et al., *Nature Revs. Cancer* 2, 361-72 (2002)) and deregulated Shh signaling linked to some specific cancers, e.g. small-cell lung cancer (Watkins, D. N. et al., *Nature* 422, 313-317 (2003)) and pancreatic adenocarcinomas (Thayer, S. P. et al., *Nature* 425, 851-856 (2003); di Magliano, M. P. et al., *Nature Revs. Cancer* 3(12), 903-911 (2003)). Additionally, injection of Shh protein into ischemic limbs of adult mice increased local angiogenesis (Pola, R. et al., *Nature Med.* 7, 706-711 (2001).

Sonic hedgehog is an important cell signaling molecule expressed during embryonic development. Shh is involved in the patterning of the developing embryonic nervous system, somite and limb. The N-terminal peptide of Shh is released by autoproteolysis and functions through interactions with a multicomponent receptor complex containing the transmembrane proteins Patched (Ptc) and Smoothened (Smo). In the absence of hedgehog protein, Ptc inhibits Smo, a G protein coupled-like receptor. When Shh binds to Ptc, Smo is disinhibited and initiates a signaling cascade that results in activation of a transcription factor, Gli-1. Shh protein is expressed in key embryonic tissues such as the Hensen's node, zone of polarizing activity in the posterior limb bud, notochord, and floor plate of the neural tube. Aberrant activation of the hedgehog pathway has been reported to be associated with certain human cancers, including basal cell carcinoma.

As used herein, Sonic hedgehog antagonist or inhibitor refers to any natural or synthetic substance that decreases, inhibits or abolishes Shh activity, either directly or by affecting any step of the Shh-pathway of signal transduction which involves Patched, Smoothened and Gli. Examples of Shh antagonists include: anti-hedgehog antibodies (5E1), natural products such as the plant alkaloid cyclopamine, small molecule inhibitors such as Cur61414, peptides such as forskolin, the adenylate cyclase activator that functions via protein kinase A to activate the destruction of Ci/Gli (Williams, J. A. et al. *Proc Natl Acad Sci USA*, 100(8) 4616-4621 (2003)).

As used herein, sonic hedgehog agonist refers to any natural or synthetic substance that activates or stimulate the activity of Shh or of the Shh-signaling pathway. An example of a Shh agonist is Hh-Ag, a synthetic non-peptidyl small molecule (Frank-Kamenetsky, M. et al. *J. Biol.* 1(2) 10.1-10.19 (2002)).

As used herein, angiogenesis factor refers to a substance secreted by a tumor to induce blood vessel growth (angiogenesis). Angiogenesis is the physiological process involving the formation of new blood vessels from pre-existing vessels, while vasculogenesis is the process of blood vessel formation occurring by a de novo production of endothelial cells. Though similar, the two are different in one aspect: the term angiogenesis denotes the formation of new blood vessels from pre-existing ones, while vasculogenesis is the term used for the formation of new blood vessels when there are no pre-existing ones. Tumors induce blood vessel growth (angiogenesis) by secreting various growth factors (e.g. Vascular Endothelial Growth Factor or VEGF). Growth factors, such as bFGF and VEGF can induce capillary growth into the tumor, supplying required nutrients and allowing for tumor expansion. Thus angiogenesis is a necessary and required step for the transition of tumors from a dormant state to a malignant and perhaps even for the spread of a tumor, or metastasis. Angiogenesis factors are also secreted by macrophages and stimulate neovascularization in healing wounds.

As used herein, anti-angiogenesis factors (or angiogenesis inhibitors) are natural and synthetic substances that inhibit angiogenesis. Examples of natural anti-angiogenesis factors include angiostatin, endostatin, and tumstatin. Angiostatin is a natural anti-angiogenesis factor that is currently in clinical trials for its use in anticancer therapy. It blocks the growth of new blood vessels. Angiostatin is a 57 kDa multimodular fragment of a larger protein, plasminogen. Endostatin is a naturally-occurring chemical in the human body that also serves as an anti-angiogenesis agent. Similar to angiostatins, endostatins interfere with the binding of growth factors (such as VEGF) to angiogenesis factors. An example of a synthetic anti-angiogenesis factor is Avastin®. Avastin® (bevacizumab; Genentech) is a monoclonal antibody directed against an isoform of VEGF. Avastin® interacts with VEGF, thereby inhibiting the binding of VEGF to the receptors that promote angiogenesis.

As used herein, the term stem cell refers to unspecialized human or animal cells that can produce mature specialized body cells and at the same time replicate themselves. Stem cells include embryonic stem cells and adult stem cells. Embryonic stem cells are derived from a blastocyst (the blastula typical of placental mammals), which is very young embryo that contains 200 to 250 cells and is shaped like a hollow sphere. The stem cells themselves are the cells in the blastocyst that ultimately would develop into a person or animal. "Adult" stem cells are derived from the umbilical cord and placenta or from blood, bone marrow, skin, and other tissues. The similar embryonic germ line cells come from a fetus that is 5 to 9 weeks old and are derived from tissue that would have developed into the ovaries or testes. Stem cells could have the capacity to repair or replace damaged body tissues because stem cells are less likely than other foreign cells to be rejected by the immune system when they are implanted in the body. Embryonic stem cells have the capacity to develop into every type of tissue found in an adult. Germ line cells and adult stem cells are widely believed by many to be less versatile, although this view may be rapidly evolving and becoming less restricted as new methods for manipulating adult stem cells are discovered. Stem cells have been used experimentally to form the hematopoietic (blood-making) cells of the bone marrow and heart, blood vessel, muscle, and insulin-producing tissue.

Methods according to the invention for identifying a tumor product and for analyzing uptake or metabolism of a composition by a tumor can be adapted for use in a high throughput format. High throughput screening can include the use of arrays of agents or reagents and, optionally, various robotic devices for sample handling.

A tumor product can be isolated from a tumor using any suitable method. Methods of isolating soluble products from a tissue are well known in the art and can include, without limitation, immunoaffinity chromatography, immunoprecipitation, size exclusion chromatography, high pressure liquid chromatography, and cloning and recombinant expression using a suitable expression vector and expression host cell system. Such methods generally entail no more than routine amounts of experimentation for any given tumor product.

Methods of isolating living cells from a tissue are also well known in the art and can include, without limitation, fluorescence-activated cell sorting, immunobead affinity separation, enzyme-linked immunosorbent assay (ELISA), and the like.

The invention in certain aspects involves sampling arterial influx to a tumor and sampling venous efflux from the tumor. As disclosed herein, the vasculogenic tumor of the invention can resemble an organ with a paired artery and vein serving as the sole or major vascular connection to a host in which it resides. These vascular structures can be sufficiently large as to make it possible to sample contents of the vascular (arterial) influx to the tumor and the vascular (venous) efflux from the tumor. Such sampling is not feasible for tumors having an angiogenic program, for which there are no such large vascular structures supplying and emanating from such tumors.

Arterial influx as used herein refers to a fluid, usually blood, contained or coursing within an artery. Venous efflux as used herein refers to a fluid, usually blood, contained or coursing within a vein.

As used herein, sampling arterial influx to a tumor refers to gaining access to and contacting the blood or other fluid contained or coursing within an artery supplying the tumor. In one embodiment the tumor is a tumor characterized by a vasculogenic program. The sampling can but need not include removing an amount of fluid contained within or flowing through the artery supplying the tumor. Thus sampling can be performed in one embodiment by the introduction of a probe into the lumen of the artery and then acquiring information in situ via the probe. In one embodiment sampling can be performed by introducing a needle or catheter into the lumen of the artery and withdrawing a volume of blood or other fluid contained within or flowing through the artery. The blood or fluid so obtained can then be processed in vitro to obtain information about compositions in the withdrawn sample. The sampling arterial influx can be performed substantially coincident with sampling venous efflux, or it can be performed separate in time from sampling venous efflux.

As used herein, sampling venous efflux to a tumor refers to gaining access to and contacting the blood or other fluid contained or coursing within a vein draining the tumor. In one embodiment the tumor is a tumor characterized by a vasculogenic program. The sampling can but need not include removing an amount of fluid contained within or flowing through the vein draining the tumor. Thus sampling can be performed in one embodiment by the introduction of a probe into the lumen of the vein and then acquiring information in situ via the probe. In one embodiment sampling can be performed by introducing a needle or catheter into the lumen of the vein and withdrawing a volume of blood or other fluid contained within or flowing through the vein. The blood or fluid so obtained can then be processed in vitro to obtain information about compositions in the withdrawn sample. The sampling venous efflux can be performed substantially coincident with sampling arterial influx, or it can be performed separate in time from sampling arterial influx.

In various aspects the methods of the invention include measuring an amount of a composition in the arterial influx and an amount of the composition in the venous efflux. The composition to be measured can be any composition of interest. In various embodiments the composition to be measured can be a tumor product, a cytokine, a growth factor, a morphogen, an angiogenic factor, an anti-angiogenic factor, a hormone, a nutrient, a metabolic waste product, a drug, a drug metabolite, a drug candidate, a test agent, an imaging agent, a labeling agent, a cell, and any combination thereof.

The measuring can be performed using any method suitable for that purpose. The method of measurement will be selected based at least in part on the identity or type of composition to be measured. Those of skill in the art will be able to determine which methods are suited for measuring particular compositions or types of compositions. The methods may involve the use of any one or combination of techniques involving chemical reagents, antibodies, bioassays, mass spectrometry, nuclear magnetic resonance spectroscopy, nucleic acid sequencing, protein sequencing, microarrays, hybridization techniques, and fluorescence-activated cell sorting, to name but a few.

As used herein, measuring an amount refers to measuring an absolute amount or a relative amount. An absolute amount can be an amount expressed in terms of mass, moles, activity, volume, temperature, pressure, and the like. A relative amount can be an amount expressed in terms of concentration, percent, relative activity, and the like.

An aspect of the invention includes the step of identifying a composition as a tumor product when the amount of the composition in the venous efflux exceed the amount of the composition in the arterial influx. The amount of the composition in the venous efflux exceeds the -amount of the composition in the arterial influx when there is a measurable excess amount in the venous efflux as compared to the amount in the arterial influx. In various embodiments the measurable excess represents at least 5, 10, 15, 20, 25, 30, 40, 50, 60, 70, 80, 90, or 100 percent of the influx amount.

In an embodiment the composition to be measured is a drug or a drug metabolite. As used herein, a drug refers to a composition with pharmacological activity. Many drugs are small molecules, i.e., molecules with molecular weight less than or equal to about 1.5 kDa. Not all drugs are small molecules, however, as drugs also include biologics such as antibodies and other macromolecules prepared by recombinant techniques. Drugs include formulated as well as unformulated drugs. Drugs also include agents approved for clinical use as well as agents not currently approved for clinical use. The list of drugs is enormous and includes, without limitation, drugs categorized as abortofacients, analgesics, anesthetics, antibodies, anticholinergics, anticonvulsants, antidiabetic agents, antidotes, antihistamines, anti-infectives, antimalarials, antineoplastics, antiparkinsonian agents, appetite suppressants, biologicals, blood modifiers, bone metabolism regulators, cardiovascular agents, central nervous system stimulants, central nervous system depressants, cholinesterase inhibitors, contraceptives, diuretics, enzymes, gastrointestinal agents, hormones, immunomodulators, immunosuppressives, leukotriene maodulators, mast cell stabilizers, migraine preparations, muscle relaxants, nonsteroidal anti-inflammatory agents, parasympatholytics, parasympathomimetics, prostaglandins, psychotherapeutic agents, sedatives, steroids, sympathomimetics, vaccines, vasodilators, and vitamins.

In one embodiment a drug is an anti-cancer agent. Anticancer agents include chemotherapeutic agents, cancer immunotherapeutic agents, and cancer vaccines. Anticancer agents may be used alone or in combination with radiation and/or surgical procedures to treat a tumor or cancer. As used herein, an "anti-cancer agent" refers to an agent which is administered to a subject for the purpose of treating a cancer. As used herein, "treating cancer" includes preventing the development of a cancer, reducing the symptoms of cancer, and/or inhibiting the growth of an established cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951 f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS- 182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/

Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphalan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26), and Vindesine sulfate, but it is not so limited.

The immunotherapeutic agent may be selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab, and ImmuRAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus, and ImmuCyst/TheraCys, but it is not so limited.

As used herein, "effective amount" refers to any amount that is necessary or sufficient for achieving or promoting a desired outcome. In some instances an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

As used herein, the term "subject" refers to a vertebrate animal. In one embodiment the subject is a mammal. In one embodiment the subject is a human. In other embodiments the subject is a non-human vertebrate animal, including, without limitation, non-human primates, laboratory animals, livestock, domesticated animals, and non-domesticated animals.

As used herein, the term "treat" as used in reference to a disorder, disease, or condition means to intervene in such disorder, disease, or condition so as to prevent or slow the development of, to prevent, slow or halt the progression of, or to eliminate the disorder, disease, or condition.

EXAMPLES

Example 1

Tumor-Induced Arteriogenesis

Figure 1B:
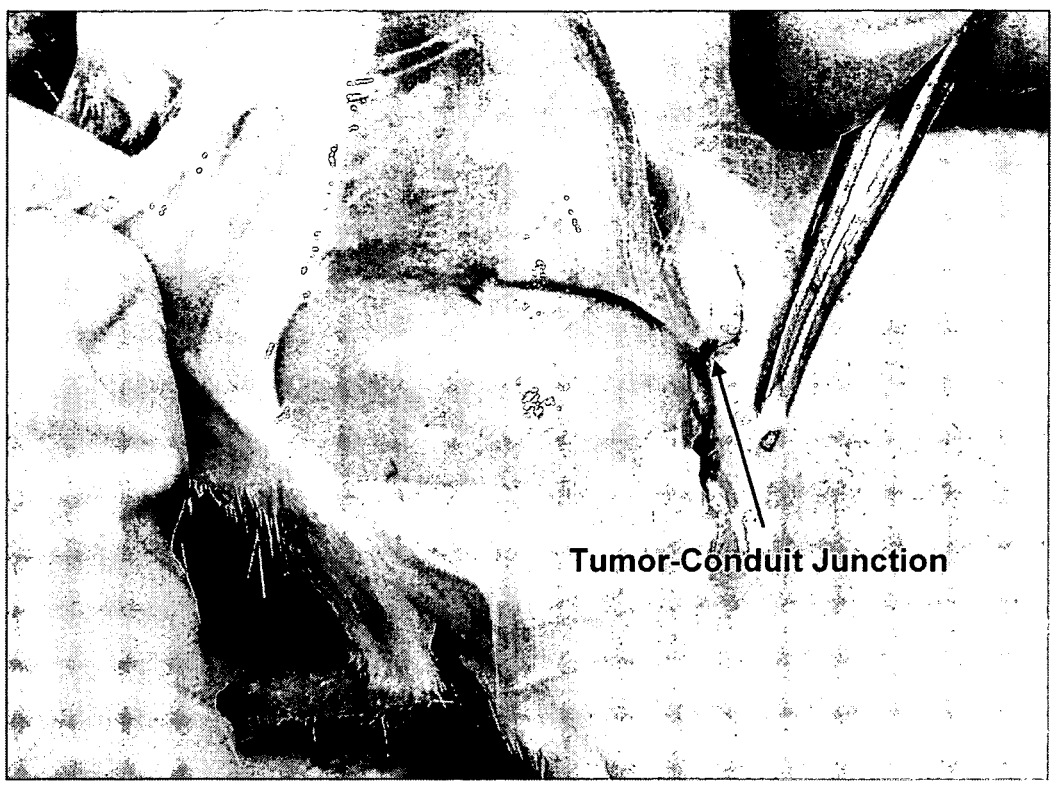
FIG. 1D shows angiograms of tumor-bearing and control animals. Angiogram on the left shows the arterial system of a SCID mouse with a liposarcoma xenograft. A main artery supplying the tumor is shown (arrow). It forms a junction with the aorta at the level of the renal arteries. Its gauge is comparable to the femoral artery. Angiogram on the right shows the arterial system of a control SCID mouse.
FIG. 1E) is a bar graph depicting the widths of representative arteries, veins, and nerves in induced and normal tissues. Shown are widths of arteries, veins, and nerves in fascia induced by the tumor, along with normal counterparts at selected sites in control (non-tumor-bearing) animals. Widths were determined in each case by measuring serial sections, and this was repeated for 30 animals (in induced fascial tissue and in the skin and back adjacent to the spine) or for 20 animals (renal artery and vein). Measured structures in the induced tissue include veins, arteries and nerves in the fascial sheath and nerves in the fascia at the tumor interface. Normal structures measured include: 1) nerves in the skin of control animals at the site where tumors were implanted in the test animals; 2) nerves in tissue dorsal to the spine; 3) the renal artery; and 4) the renal vein. Errors are 95% confidence intervals for the mean.
Figure 1C:
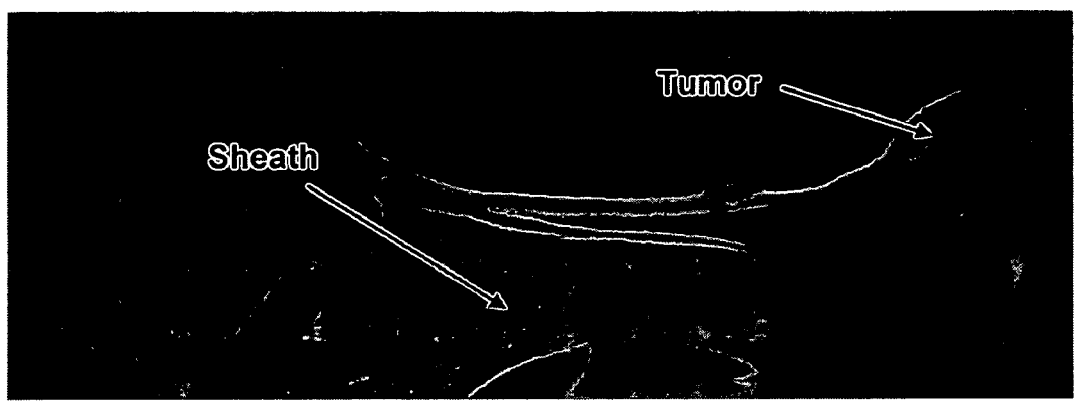

Intact human liposarcoma pieces, 1 mm$^3$, were implanted subcutaneously in mice. Implantation of a tumor piece, rather than injection of tumor cells, was used to: 1) provide local sequestration rather than interspersion of tumor cells within host tissue; 2) provide a significant isolated source of angiogenic factors to promote homing of the neovasculature; and 3) preserve the important tumor-stromal/tumor-cell architecture necessary to maintain inter-tissue signaling (Hlatky, L. et al., Cancer Res. 54, 6083-6086 (1994); Barcellos-Hoff, M. H. et al, Radiat. Res. 156(5), 618-627 (2001)). The best response was obtained when xenografts were positioned mid-dorsally on the lower back. Well-delimited tumors developed between the skin and muscle. Upon dissection the tumors were easily freed from adjacent tissue with minimal bleeding, attesting to their bounded, organ-like delimitation and vascular accommodation (FIG. 1A). The tumors elicited large-gauge arteries and veins which linked them to the host vasculature through a fascial bridge (FIG. 1C) that has no analog in control mice. The experiments yielded neovasculature (arteries and veins) of >30 mm in length between the tumor and the abdominal wall in the mouse. These vessels tracked within the fibroadipose fascia (FIG. 1B) lying external to the abdomen, loosening the fascial cohesiveness along the track of the vessels and up to their point of entry into the tumor. The fascial sheath supporting the vascular conduit consisted of connective tissue elements, including fibroblasts, collagen, adipocytes, histiocytes and mast cells. The conduit was easily freed from the adjacent skin and muscle (FIG. 1C). The majority of the xenografts implanted in this manner resulted in well-delimited tumors with substantial artery-vein conduits. Arteriogenesis was also detected in the extension of this artery within the abdominal wall and peritoneal cavity. This was not the case if the tumor was injected as a cell suspension (preserving the full range of cell types present in the tumor). When injected as a suspension, tumors grew poorly, invaded local tissues including the skin, produced a large proportion of smaller extratumoral vessels, and yielded no major artery-vein conduits. Sham surgery, conducted to examine if growth factor production secondary to the implant surgery was sufficient to induce arterialization, failed to induce any vessels of significant size directed to the site. Sham surgeries consisted either of the subcutaneous implantation of a piece of biologically inert clinical-grade implant material (e.g. testicular implant material, Silimed) of similar size (1 mm$^3$) to the tumor implants, or of the simple wounding and suturing of an animal.

Figure 1D:
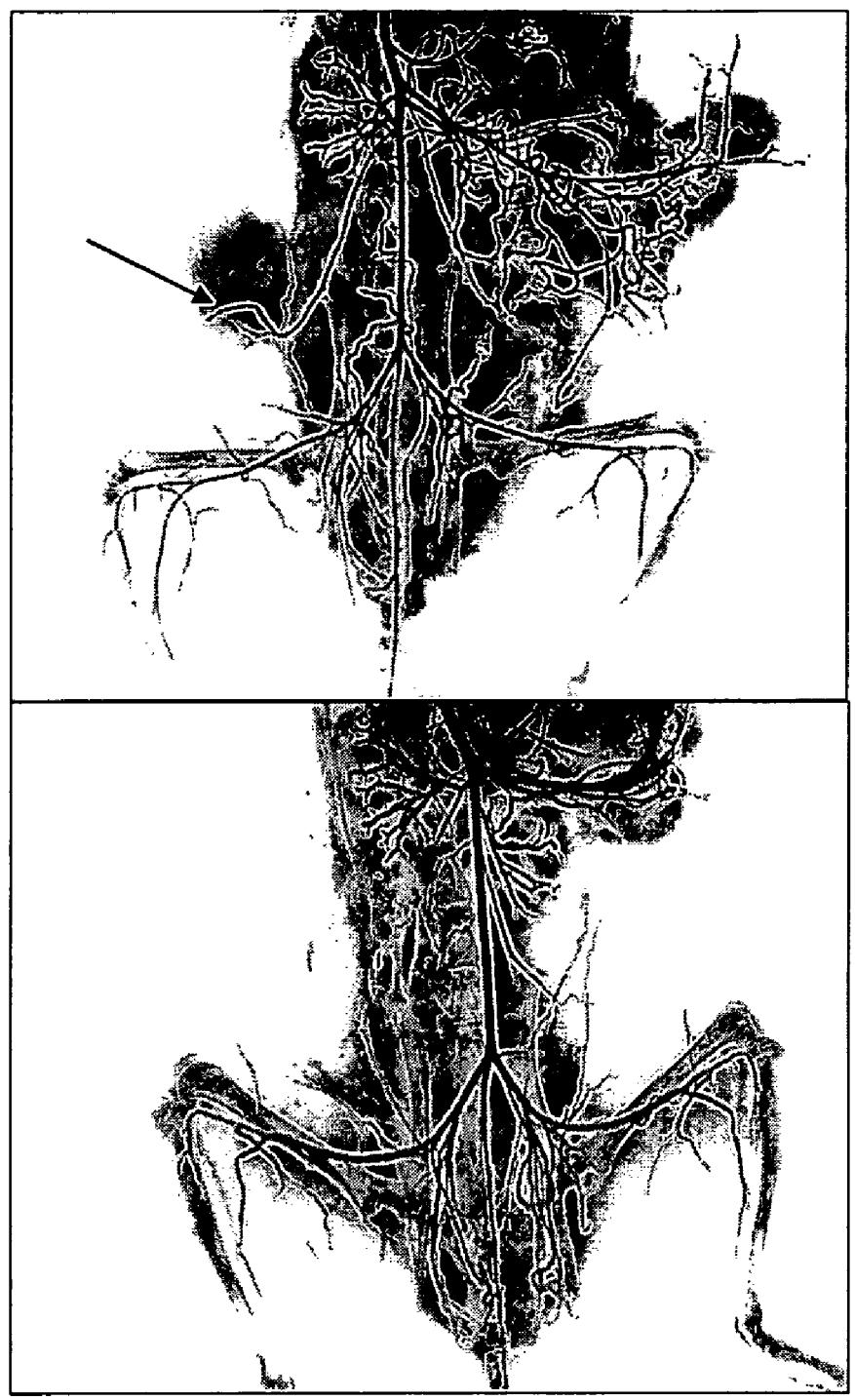
Figure 1E:
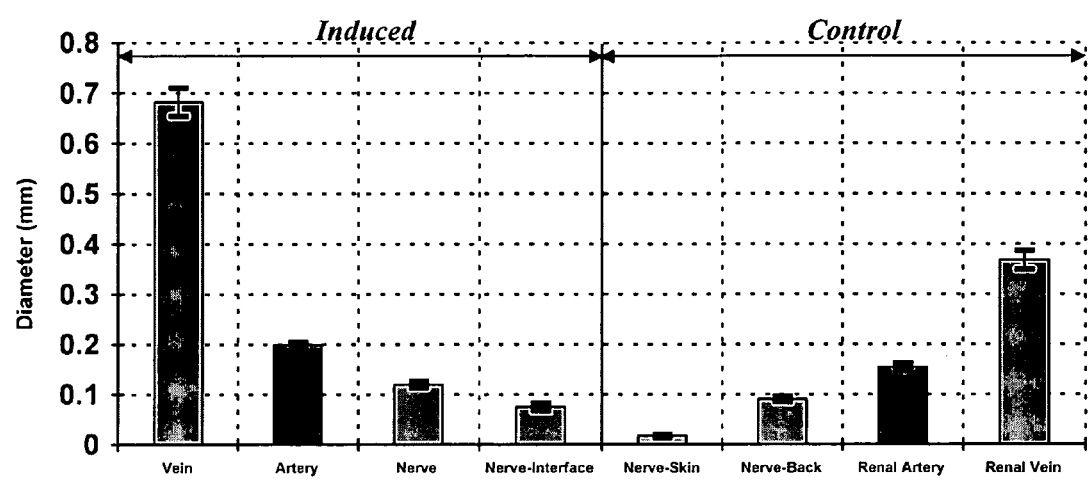

Arterial networks in the mice were visualized via angiograms following barium gel injection. For animals with implanted liposarcoma pieces, the arterial conduit to the tumors resembled that to organs (FIG. 1D). It is noted that for the tumor-bearing animal, an artery from the aorta near the renal arterial branch homed to the tumor, extending through the abdominal wall of the animal. The length of the artery between the point of penetration of the abdominal wall and the tumor reached ~30 mm. Additionally, the arterial gauges were seen to elaborate to a size comparable to that of the femoral artery (FIG. 1 D,E), as confirmed by dissection (FIG. 1 A). Angiograms of control mice showed no such artery though the abdominal wall. Unlike the classic randomly-oriented and tortuous vasculature induced within tumors, these experiments demonstrated directed, large-gauge arteries and veins induced outside the tumor. Upon reaching the tumor site, noticeable branching into smaller vessels occurs (FIG. 1A). Inside the xenografts a classic tumor vasculature was detected using antibodies to standard endothelial and smooth muscle cell markers, platelet endothelial cell adhesion molecule PECAM-1 (CD-31), CD34 (Hlatky, L. et al., *J. Natl. Cancer Inst.* 94, 883-893 (2002)) and alpha smooth muscle actin (αSMA).

Figure 2A:
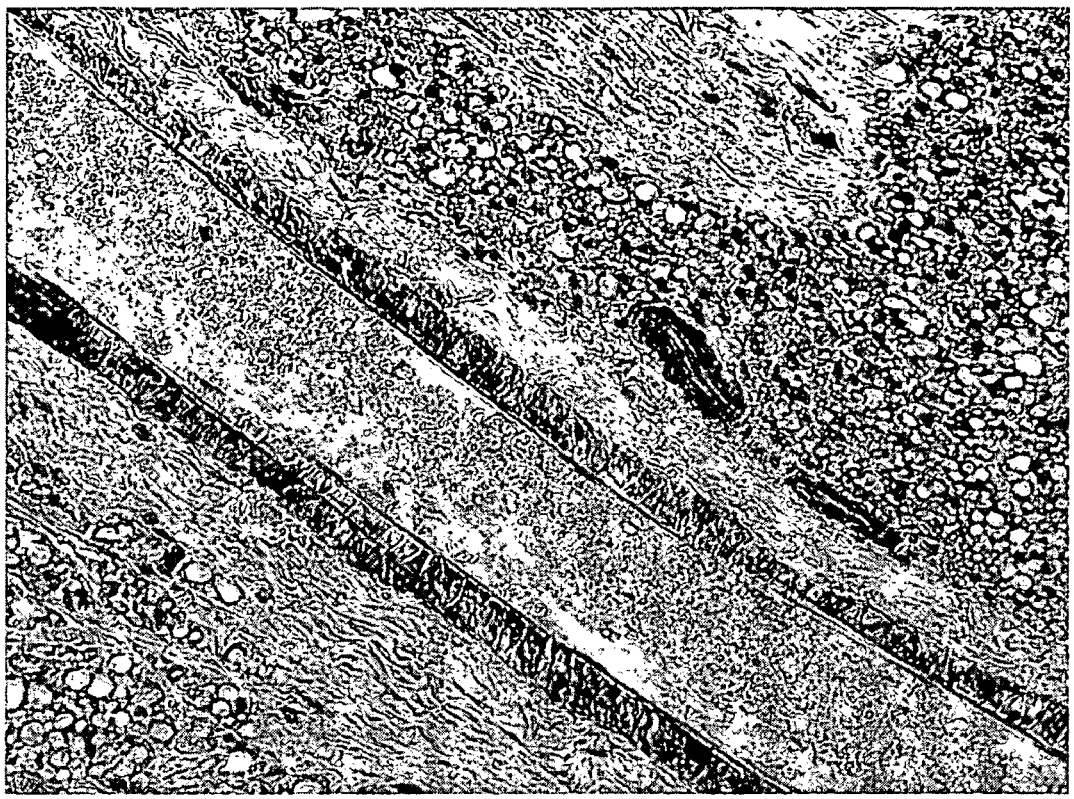
FIG. 2 shows cross-sections of tumor conduit arteries and veins. The artery and vein exhibit properties of mature, functional vasculature. A) Shown is the well-organized, layered structure of the artery in the region of the conduit between the tumor and abdominal wall. The muscular media is highlighted with smooth muscle actin immunostain (reddish brown). An adventitial layer that does not stain is also evident. External to the adventitia is fibro-adipose tissue. Endothelial cells are seen to line the uniform lumen. B) In cross-section is shown the classic, serpentine structure of the elastic lamina in the fully-formed artery, with the smooth muscle actin-labeled muscular media surrounding. A final adventitial layer is displayed. By contrast, the vein is thin-walled, with a relatively large lumen. C) Longitudinal section of artery and vein in a tumor conduit. This section, which passes into, out of, then back into the arterial lumen, shows smooth muscle actin immunostain labeling in the muscular walls of the artery and vein. An accompanying nerve is also present. D) This section follows serially from that in FIG. 2C and is stained for elastin (black) and collagen (red). Three layers in the arterial wall are evident. The internal and external elastic laminae of the artery are well-defined by the elastin stain (black). Perivascular adventitial collagen stains red. In between is the muscular media. E) Cell proliferation in the artery and nerve in the tumor conduit. Ki-67 immunostain shows labeling of endothelium and smooth muscle cells as well as cells in the surrounding connective tissue and within the nerve. Section counterstained with hematoxylin and eosin (H&E) (4×).
Figure 2B:
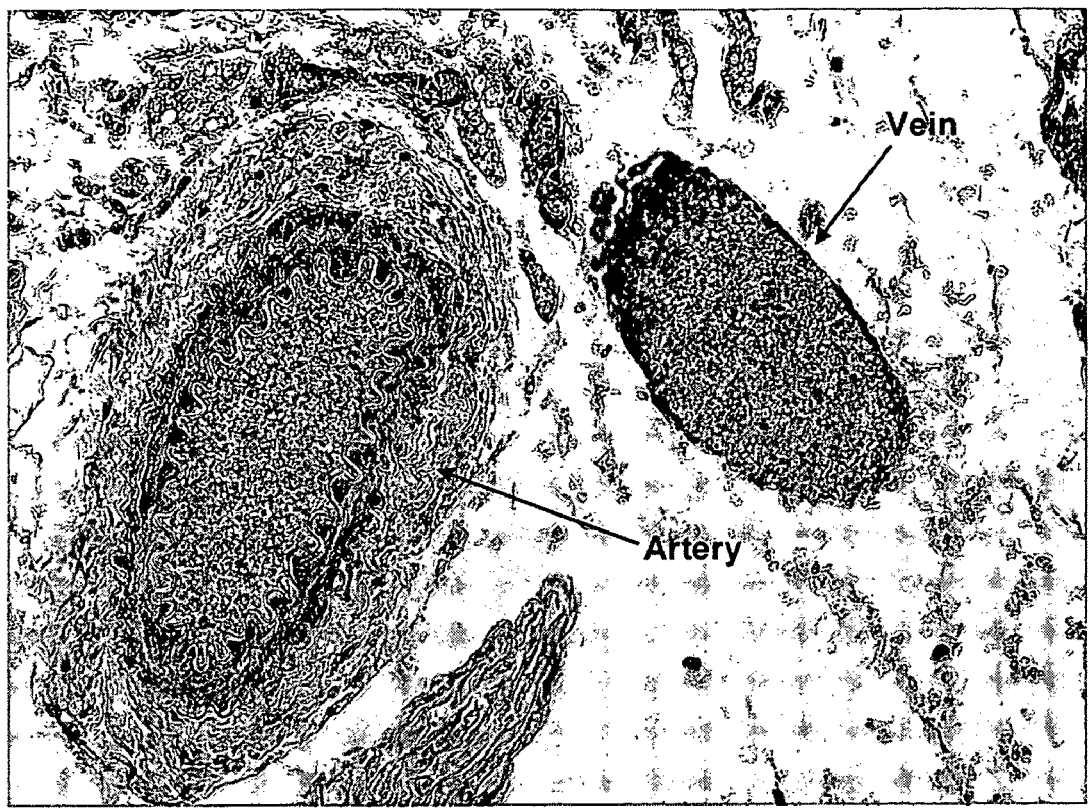
Figure 2C:
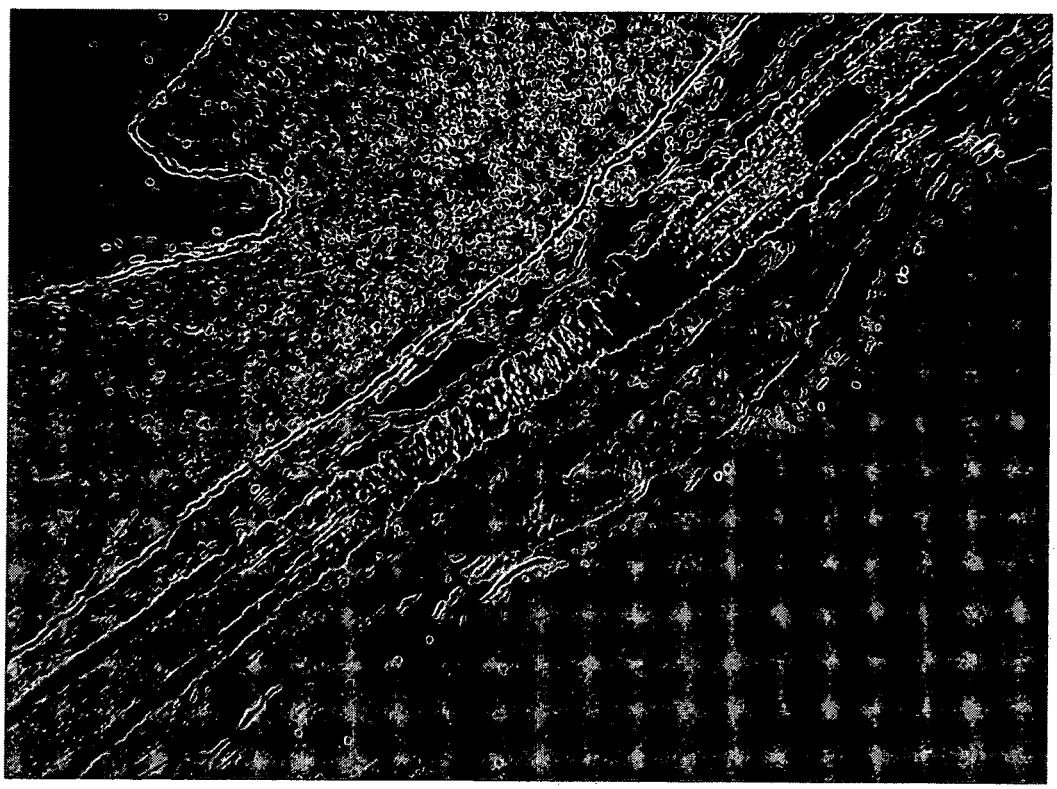
Figure 2D:
Figure 2E:
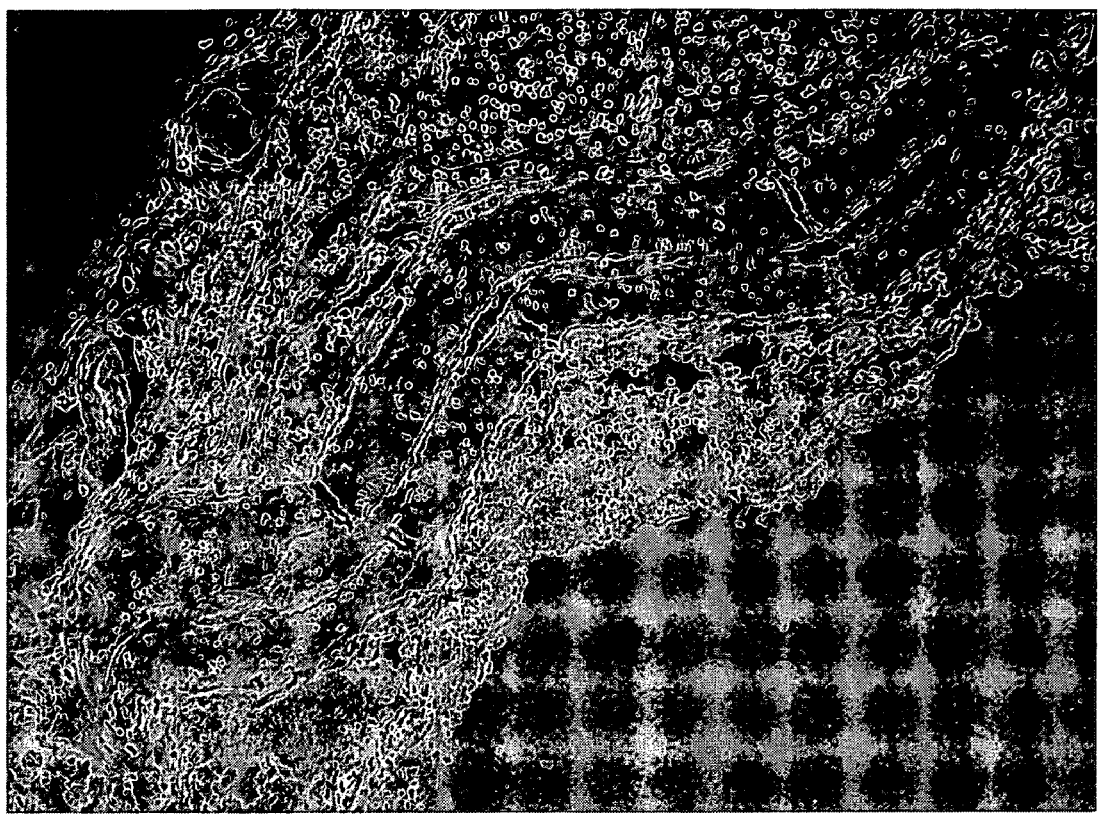

As confirmed by structural, flow dynamic, and immunohistochemical criteria, the artery and vein of the vascular conduit exhibited properties of mature functional vasculature (FIG. 2A-D). Induced arteriogenesis was demonstrated by the well-developed wall structure of the arteries. In the arterial cross-sections, a characteristic serpentine internal elastic lamina, muscular media, external elastic lamina and adventitia were present, and the wall-thickness-lumen ratio was appropriate, suggesting full viscoelastic and vasomotor functionality (FIG. 2B). Pulsatility and the uni-directional flow in the arteries was established by two-color directional Doppler imaging. Immunohistochemically, the densely αSMA-stained media within the walls of the large vessels was consistent with identification of these vessels as mature arteries and veins (FIG. 2A,B,C). Elastin staining demonstrated the normally prominent internal and external elastic laminae in the arteries and the normally less well-developed elastic layers in the vein (FIG. 2D). Interestingly, despite these impressions of vascular maturity, proliferation data indicated ongoing arteriogenic development. Cell proliferation within the artery and vein was assessed via proliferating cell nuclear antigen (PCNA) and Ki-67 (MIB 1), a nuclear protein expressed in all cycle phases except $G_0$. Unlike normal adult vasculature which is essentially non-proliferating (Hobson, B. et al., *J., Br. J. Cancer* 49(4), 405-413 (1984); Folkman, J. et al., New York: Cold Spring Harbor Laboratory Press; p. 1-17 (1998)), labeling confirmed proliferative activity in both endothelial and smooth muscle cells of the arteries and veins within the conduits, in addition to proliferating cells in the surrounding connective tissue (FIG. 2E). Cell proliferation was detected to be highest near the tumor. The endothelium of the artery and vein were derived from the host and not from endothelial cells of the implanted tumor. This was determined by implanting tumors in mice transgenically altered with green fluorescent protein, GFP, driven by a Tie-2 promoter to identify host endothelium.

Example 2

Tumor-Induced Neurogenesis

Figure 3A:
FIGS. 3A and B are cross-sections of the tumor conduit neurovascular bundle. A) Neurovascular bundle in the tumor conduit. The localization and orientation of the nerves was demonstrated by immunodetection of axons using an antibody to neurofilament. Section counterstained with H&E. B) Nerve presence in the tumor-conduit interface. Multiple nerve sections are detected by S-100 immunostain (brown). Section counterstained with H&E (20×).
Figure 3B:
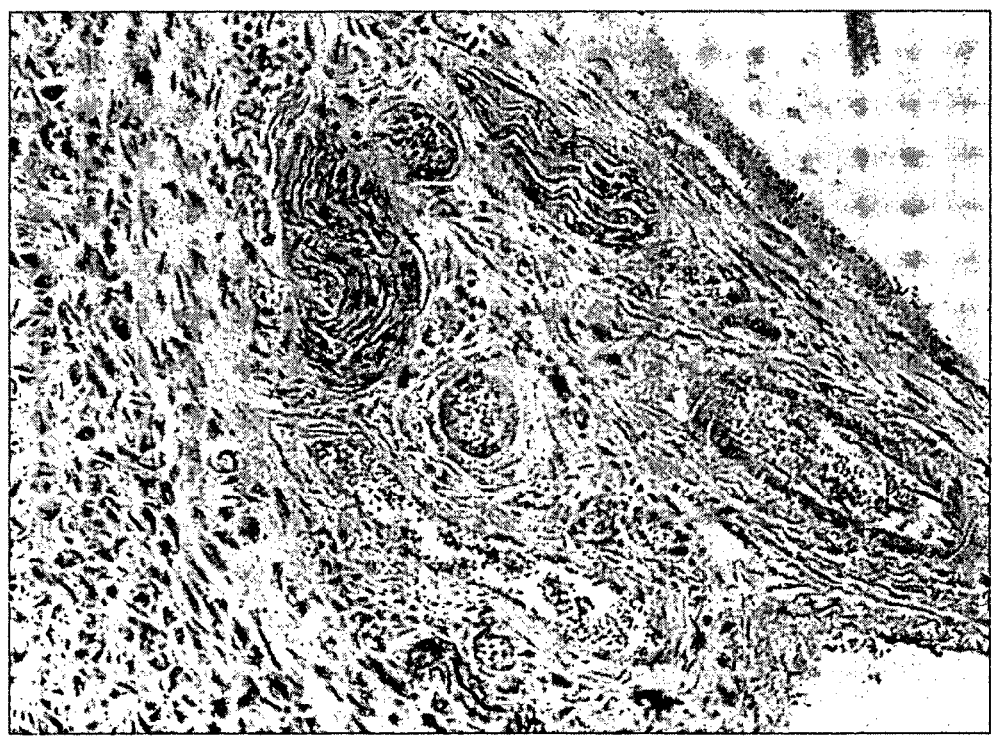
FIG. 3C shows a schematic of the tumor with its induced conduit and a bar graph depicting the quantification of tumor-induced nerve presence. Shown is a schematic of the tumor with its induced conduit, containing a neurovascular bundle embedded in a fibro-adipose support tissue. The conduit extends from the tumor to the abdominal wall (~30 mm—Region 2), traverses the wall (Region 3), and continues on (Region 4) to connect to the aorta near its junction with the renal arteries. Quantified for each region is the 'nerve presence index'—the average ratio of nerve tissue area to total tissue area measured in each microscope field. In the neurovascular bed at the tumor-conduit interface, the nerve index was highest at 6.98%±1.00, falling off with distance from the tumor to the wall (3.49%±1.52 in Region 2, and 0.39%±0.11 in the abdominal wall). The nerve index then increased slightly in Region 4 (0.65%±0.17). The skin overlying the tumor showed negligibly small nerve detection. Additionally shown are the nerve indices for control, non-tumor-bearing animals (skin: 0.07%±0.05 and abdominal wall: 0.40%±0.20). For statistical accuracy, up to 100 imaged fields (80× magnification) were averaged to obtain the measurements in each region.

The implanted xenografts in this experiment induced directed nerves. In the fascial bridge connecting the tumor to the abdominal wall, which notably has no analog in the control mouse, nerves were seen to track parallel to the vasculature. The nerves associated with the arteries in a manner analogous to nerve routing in normal development (Martin, P. & Lewis, J. Origins of the neurovascular bundle: interactions between developing nerves and blood vessels in embryonic chick skin. *Int. J. Dev. Biol.* 33(3), 379-387 (1989); (Mukouyama, Y. S. et al., *Cell* 109(6), 693-705 (2002)); (FIG. 2C). Nerve localization and orientation was demonstrated by immunodetection of axons using an antibody to neurofilament (FIG. 3A). Enveloping Schwann cells were positively detected via an antibody to S-100 (FIG. 3B). FIG. 2C shows a neurovascular bundle, with nerve, artery and vein marked, as it homes to the xenograft. Labeling with neurofilament and S-100 verified the presence of nerve within the entire conduit. These nerves were often large (~0.12 mm in diameter in paraffin sections—FIG. 1E). Infrequently, nerves were covered by a myofibroblast coat as identified by αSMA staining. Smooth muscle actin staining has been found in contractile myofibroblasts in the perineurium surrounding fascicles containing collections of nerve fibers comprising functional nerves (Chamberlain, L. J. et al., *J. Comp. Neurol.* 417(4), 415-430 (2000)). The axially-oriented myofibroblasts are believed to create axial tension and align collagen fibers to facilitate the elongation of regenerating axons at a transection site.

Figure 3C:
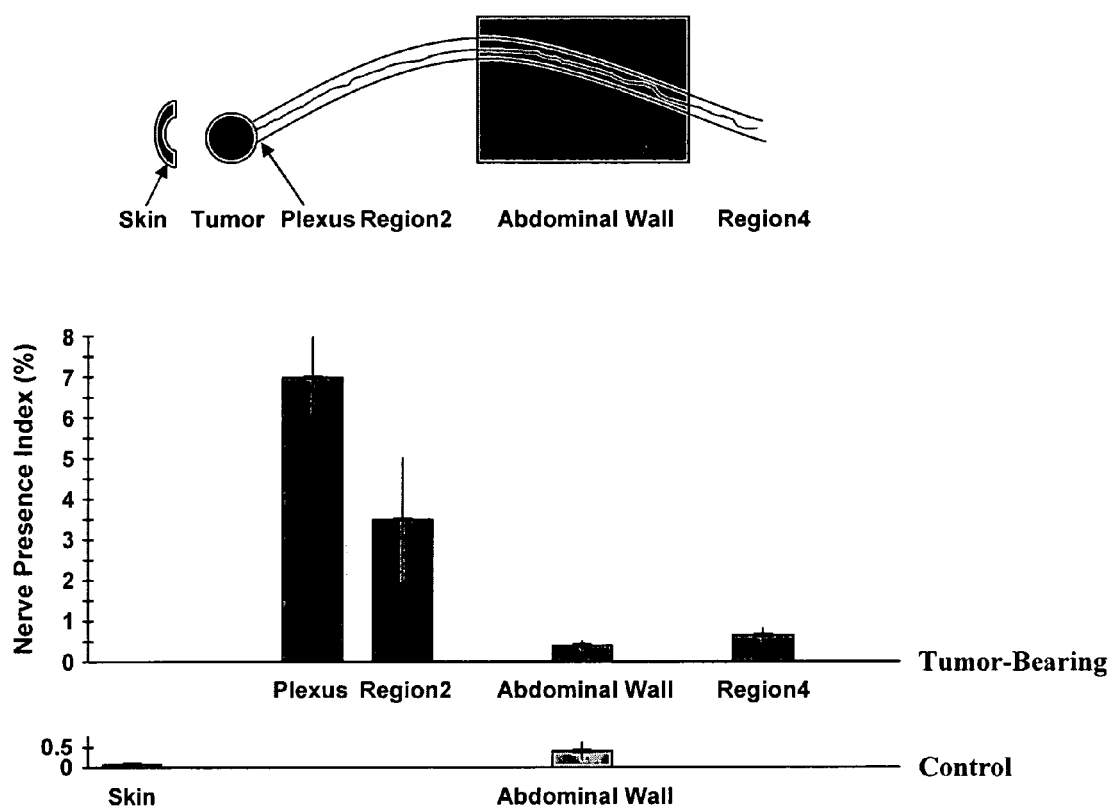

At the tumor-conduit interface, the nerves and vessels branched, forming a bed of high vessel and nerve track density (FIG. 3B). Again, close association and parallel orientation of the large neovessels and nerves was observed. To examine the extent of neurogenesis that accompanied tumor growth, nerves along the neurovascular conduit and in the neurovascular bed at the base of the tumor were quantified using immunohistochemistry in combination with digitized imaging. Scoring of peripheral nerves was based on the simultaneous demonstration of axons labeling with neurofilament and Schwann cells labeling with S-100. For the quantification of nerve areas, S-100 labeling was imaged. Ratios of nerve area/tissue area were calculated yielding a "nerve presence index" measure. To capture the dependence of nerve presence with position along the conduit, the entire conduit was scanned, following its extension back to the aorta. The total conduit between the tumor and aorta was divided into four distinct regions: Region-1 (the tumor-conduit interface) directly adjacent to the tumor; Region-2 between the tumor-conduit interface and the abdominal wall (~30 mm); Region-3 within the abdominal wall; and Region-4 between the abdominal wall and the insertion point of the conduit artery into the aorta (FIG. 3C). In Region-1, the nerve index was 6.98%±1.00, in Region-2, 3.49%±1.52, in Region-3, 0.39%±0.11, and in Region-4, 0.65%±0.17. It is noted that considerable nerve presence was induced by the tumor, with 5-10-fold higher nerve presence indicated in the newly-generated portion of the conduit outside the abdominal wall, compared to that visualized within the animal and in the abdominal wall. For control mice without tumors, the nerve index was quantified in the two tissues which lie directly adjacent to the site where tumors would be implanted: 1) the underside of the skin (0.07%±0.05), and 2) the abdominal wall (0.40%±0.20). A 100-fold increase in nerve presence is seen in the interface region around the tumors as compared to the skin in non-tumor bearing mice. The nerve index in the abdominal wall was the same in both the tumor-bearing and control animals (0.39%±0.11 and 0.40%±0.20). Up to 100 imaged fields were averaged to obtain the measurements in each region.

In adult nerves, Schwann cells are quiescent with heterochromatin-rich nuclei. However, in regenerating nerve, Schwann cells proliferate and form columns that serve as scaffolds for regenerating axons by expressing adhesion molecules on the surface plasma membrane and producing various tropic factors for regenerating axons (Evans, G. R., *Semin. Surg. Oncol.* 19(3), 312-318 (2000)). Proliferation within the nerves induced in this experiment was assessed via the expression of both PCNA and Ki-67. Ki-67, widely used to detect proliferation in tumor and vascular studies, has recently been used as a proliferation marker in adult neurogenesis (Kee, N. et al., *J. Neurosci. Meth.* 115(1), 97-105 (2002)). Positive Schwann cell labeling was detected with both Ki-67 (FIG. 2E) and PCNA staining, indicating proliferation. Supporting these observations, H&E revealed Schwann cells which appeared plump and active with light chromatin staining, indicative of proliferative status.

Example 3

Sonic Hedgehog Signaling is Instrumental in Tumor-Driven Adult Neurogenesis This experiment was a study of the role of the embryonic signaling molecule Sonic Hedgehog (Shh) in driving the neurogenic and arteriogenic processes induced by the implanted tumors in these adult mice. Sonic hedgehog, a key developmental morphogen in vertebrates, plays an essential role in the development of neuronal cells and tissues in both the peripheral and central nervous system (Lum, L. et al., *Science* 304, 1755-9 (2004)). In addition, it is central in determining dorsal-ventral polarity of the neural tube (Chiang, C. et al., *Nature* 383, 407-13 (1996); Marti, E. et al., *Nature* 375, 322-325 (1995); Ingham, P. W. et al., *Genes Devel.* 15, 3059-87 (2001)) and the determination of anterior-posterior patterning of limbs. Sonic hedgehog signaling has long been considered to be active only during development. However, recent insightful reports show continued Shh activity in adult stem cells (Lai, K. et al., *Nature Neurosci.* 6(1), 21-27 (2003); Ruiz i Altaba et al., *Nature Revs. Cancer* 2, 361-72 (2002)) and deregulated Shh signaling linked to some specific cancers, e.g. small-cell lung cancer (Watkins, D. N. et al., *Nature* 422, 313-317 (2003)) and pancreatic adenocarcinomas (Thayer, S. P. et al., *Nature* 425, 851-856 (2003); di Magliano et al., *Nature Revs. Cancer* 3(12), 903-911 (2003)). Additionally, injection of Shh protein into ischemic limbs of adult mice increased local angiogenesis (Pola, R. et al., *Nature Med.* 7, 706-711 (2001)).

Figure 4A:
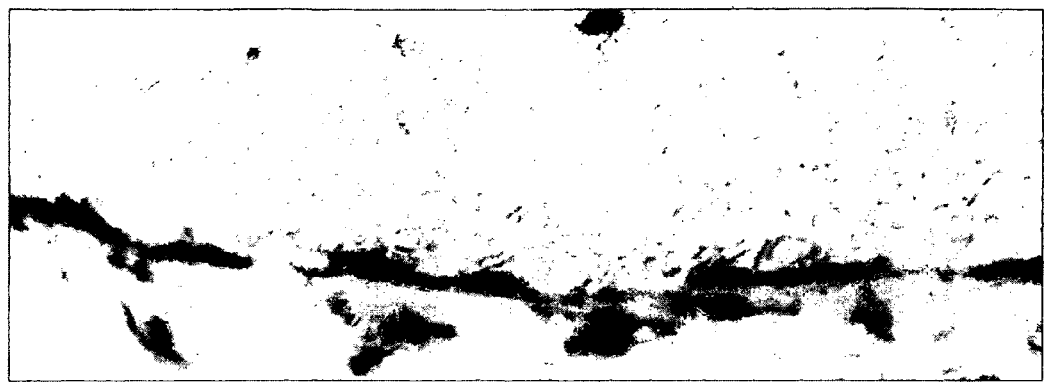
FIG. 4 shows tissue cross-sections that depict the identification and localization of cells expressing Sonic hedgehog (Shh) mRNA and protein. A) In situ hybridization with Shh, showing positively-labeled endothelial cells (blue) lining the lumen of the conduit vein (40×). B) Shh protein presence in tumor conduit structures. Shh protein staining in an artery/vein cross-section. Positive labeling (brown) is evident in adipocytes of the fascial bridge and in smooth muscle cells in the muscular media of the artery (40×). C) Shh protein labeling in nerve cross-sections. Strong staining is evident in the epineurium surrounding the nerves. No such labeling is seen in control non-tumor bearing mice. D) Generalized Shh protein labeling in the tumor conduit. A diffuse, granular labeling for Sonic hedgehog protein is seen in mesenchymal areas in the conduit adjacent the neurovascular bundles. This labeling appears to be identifying secreted Shh protein contributing to a morphogenic gradient, similar to what has been observed in embryonic contexts.
Figure 4B:
Figure 4C:
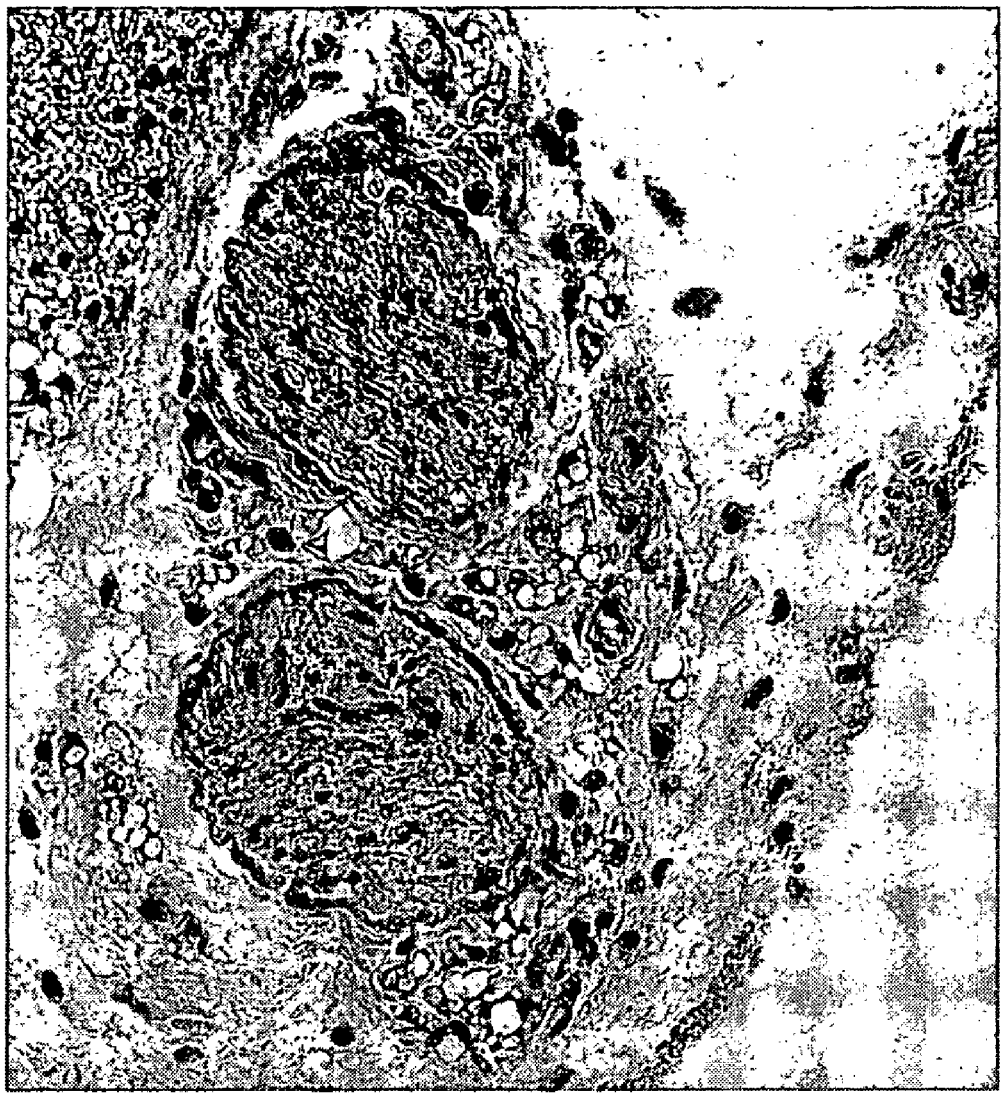
Figure 4D:
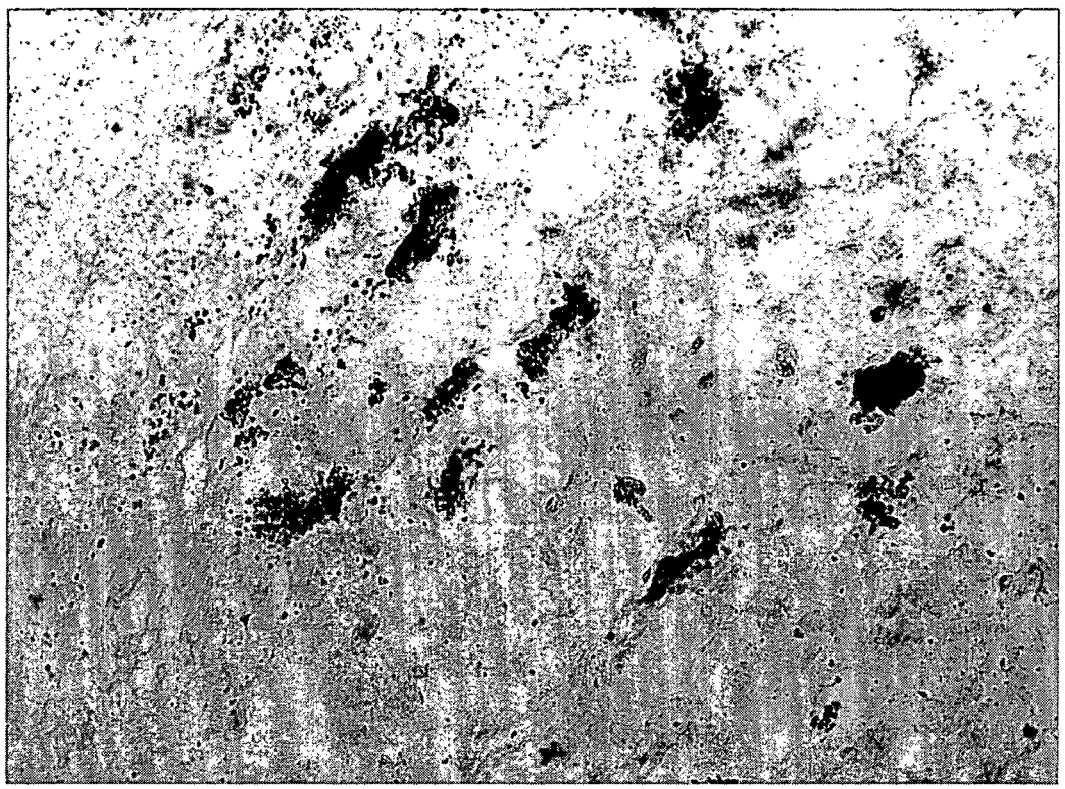
Figure 5:
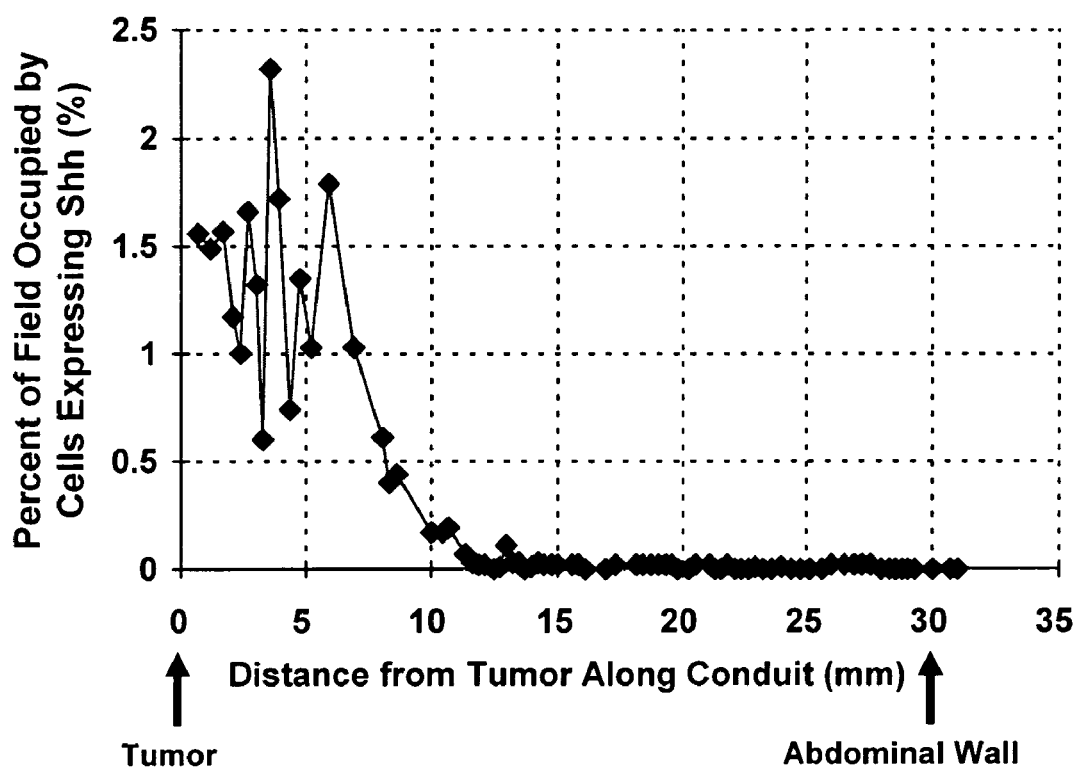
FIG. 5 is a diagram that depicts the global pattern of Shh mRNA expression over the neurovascular conduit. In the portion of the tumor conduit extending from the tumor to the abdominal wall (~30 mm), Shh mRNA expression was quantified using digitized densitometric imaging. The tumor with conduit was embedded in paraffin, sectioned longitudinally, and mounted on a microscope slide. Using the successive x-y positions of the midline of the curved conduit for each 400 μm step in the x-position, distance along the conduit from the tumor was calculated. Measured as a function of this distance along the conduit was the ratio of the hybridization signal area detected to the total tissue area in each microscope field. For each x-step, ten adjacent fields were imaged in the y-direction (so as to cover the conduit width) and averaged to arrive at a value at that point along the conduit. The signal starts at 3.6% at the tumor-conduit interface, falling eventually to 0.1% 12 mm from the tumor.

To identify and localize cells expressing Shh message and protein, in situ hybridization and immunohistochemistry were used. Significant Shh (both mRNA and protein) was detected in the interface at the base of the tumor and in the nerve, artery and vein of the neurovascular bundles (FIG. 4A-D). Within the artery and vein Shh was detected in both endothelial and smooth muscle cells. In the nerves, Shh protein expression was pronounced in Schwann cells and in the epineurium, which also labeled strongly for CD34, (FIG. 4C). Demonstrating the highest Shh expression were various cell types in the fascial connective tissue surrounding the neurovascular structures within the conduit, including adipocytes and fibroblasts. In response to tumor implantation, cellular Shh expression throughout the whole body of the animals was also examined. Beyond those few locations where Shh is known to be found in adult mice (e.g. in hair follicles), only cells of the induced neurovascular bundle conduit and the surrounding fibro-adipocyte tissue labeled for Shh in tumor-bearing mice. To evaluate the global pattern of Shh mRNA expression over the neurovascular conduit, digitized imaging was used to quantify cellular in situ Shh expression as a function of distance along the conduit. This was accomplished using an automated scanning procedure which detected Shh hybridization signal in a montage of microscope fields covering the entire conduit length. The percentage of tissue per microscope field scoring positive for Shh mRNA decreased markedly as a function of distance from the tumor (FIG. 5). This percentage decreased from 3.6% in the tumor-conduit interface to 0.1% at 12 mm from the tumor, and decreased slowly thereafter. This suggests the signals driving the formation of the neurovascular bundle originated at the tumor site, and that a stable gradient in this signaling was established with distance from the tumor. A stable gradient of this scale is reminiscent of the morphogen gradients found in the developing embryo. Comparing the data of FIG. 5 with that of FIG. 3C, one observes that regions of the highest Shh expression coincide with those having the highest nerve presence index.

To investigate whether Shh developmental pathways played a critical role in the generation of the neurovascular bundles, Shh signaling was blocked in the early stages of tumor growth. Shh acts by inhibiting Patched (Ptc), thereby reducing the normally inhibitory effect of Ptc on Smoothened (Smo). This activates the Shh pathway. Cyclopamine, a plant alkaloid that blocks the action of Smo in the receptor complex and thus the signaling pathway of Shh, was delivered subcutaneously (following the methods of Thayer et al., 2003 (Thayer, S. P. et al., *Nature* 425, 851-856 (2003)) to tumor-bearing mice 12 days after tumor implantation. Treatment was delivered daily (50 mg/kg) for a period of 5 days. After 4 days of treatment tumor regression was observed. On day 7 following the start of treatment the mice were sacrificed and the tissue examined. Tissue from both treated and untreated tumor-bearing mice were compared. At autopsy, there was no evidence of viable tumor or of a neurovascular bundle after cyclopamine treatment. In contrast, the untreated tumor-bearing animals had established neurovascular bundles and cells in the supporting sheath expressing Shh. Sections of skin and tissue surrounding the tumor implant site after cyclopamine treatment showed only control Shh expressions (e.g. in hair follicles). These findings suggest that Shh signaling is instrumental in the maintenance of the neurogenesis and arteriogenesis process induced by the tumor, and that blocking this signaling abrogates these developmental programs.

Experimental Methods

The following experimental methods were used in the experiments described above.

Tumor Implantation

Primary human liposarcoma tumors were implanted subcutaneously as ~1 mm³ pieces in adult (8-10 week old) male and female SCID mice. The resulting tumors were then passed mouse to mouse: grown to ~1 cm, excised, and pieces reimplanted through a small incision mid-dorsally low on the back (n=50) of SCID (Massachusetts General Hospital, Boston, Mass.) or nude (Taconic Farms) mice. Animals with tumors 0.5-2 cm in diameter were sacrificed for investigation or prepared for angiograms or latex casting.

Angiograms and Latex Casting

Mice were euthanized ($CO_2$) and sternotomy performed to gain access to the thoracic cavity. A small vent in the right atrium was made, then the left ventricle flushed with 10-15 cc of PBS+heparin (1 ml) until fluid exiting the left atrium is clear. This was followed by perfusion with 4 ml of 5% formalin. Angiograms: 2cc of liquid-coat HD barium sulfate contrast suspension #149705 (Lafayette Pharmaceuticals, Lafayette, Ind.). Liver color was monitored to establish that contrast solution has entered the arteries and arterioles. Angiogram films prepared by routine x-ray. Latex Castings: 3-5 ml of orange Latex (Microfil, Flow Tech., Carver, Mass.) injected until the larger arteries were fully perfused.

Immunohistochemistry

Formalin-fixed, paraffin-embedded, sectioned (5 µm) samples. Slides treated with Proteinase K (Roche Diagnostic, Indianapolis, Ind.) at 37° C. for 15-30 min and blocking buffer (TNT from TSA biotin system kit, NEL 700A, Perkin-Elmer Life Sciences, Boston, MA) for 30 min at 25° C. Primary antibodies used: CD31 (PECAM1) and CD34 (Pharmingen, Bedford, Mass.), Ki-67 (Dako, Carpinteria, Calif.), PCNA (PC10 monoclonal, Dako), α-smooth muscle actin (Sigma), S-1 00 (polyclonal, Signet, Dedham, Mass.), elastin, neurofilament (monoclonal, Signet), and Shh sc-9024 (polyclonal, Santa Cruz Biotech., Santa Cruz, Calif.). Procedure excluding S-100, neurofilament, and elastin: Primary antibodies bind overnight at 4° C. (CD31, CD34, Shh) or 1 hr at 25° C. (PCNA, Ki-67, SMA). The secondary biotinylated antibody (Vector Labs, Burlingame, Calif.) applied for 30-40 min. Signal amplified with biotinyl tyramine amplification reagent (Perkin-Elmer Life Sciences, Boston, Mass.). Peroxidase enzyme added and linked using the ABC peroxidase standard kit (Vector) according to manufacturer's instructions. Visualization accomplished with the Vector Novar (Nova Red) substrate kit. Slides counterstained with hematoxylin. Elastin: Tissue section is overstained with a soluble lake of hematoxylin-ferric chloride-iodine. Differentiation is accomplished by the use of excess solution of ferric chloride to break the tissue-dye complex. S-100 and neurofilament: Signet Ultra-Streptavidin detection system, as per manufacturer's instructions. S-100 visualized with diaminobenzidine (DAB) substrate.

In Situ Hybridization

Samples were fixed in 4% PFA at 4° C. for 10 min, followed by 0.5×SSC for 5 min at 25° C., Proteinase K for 10 min at 37° C., 0.5×SSC for 10 min, 4% PFA for 5 min, 0.5×SSC for 5 min. It was then placed in a prehybridization buffer at 56° C. for 30 min (2 ml SDS 10%, 2 ml SSC 20%, 1 ml tRNA (10 mg/ml), 4 ml dextran sulfate (50%), 10 ml formamide, 1 ml DEPC $H_2O$, 500 µg (25 µg/ml) fish sperm DND. This was followed by treatment with a DIG-labeled riboprobe (1:50) at 55° C. overnight. RNAse A solution (20 mg/ml) was added and slide incubated 30 min at 25° C., incubated in anti DIG overnight at 4° C. (1:500 in blocking buffer), rinsed in buffer 1 for 2×10 min, then in buffer 3 for 5 min, developed in NBT/BCIP at 25° C. Sample counterstained methyl green for 3 min., dehydrated and coverslipped. For the mouse Shh probe, a 1.576 kb fragment was cloned into Eco-R1 site of Bluescript. Antisense—Sal 1 digest/T3 transcript; sense—Pst 1 digest/T7 transcript, 3 µl of 7 µg/µl DNA.

Digitized Imaging

Densitometric imaging was done using a Quantimet 570 computerized imaging facility (Leica), utilizing a Reichert-Jung Polyvar microscope integrated to a 500 Mhz processor-based parallel-tasking computer via a JVC 3-CCD camera. Morphological routines used to remove background "noise", isolate and measure vascular features, and assess antigen signal ratios. A scan pattern was set up according to the size of tissue sample to be imaged. The computer was calibrated for each magnification so that step sizes would correspond to field dimensions. Masking was done by varying the intensity-detection threshold to define the boundaries of the chromogen to be measured. Shh presence along the tumor conduit was quantified using an automated scanning procedure which detected Shh hybridization signal in 400×400 µm frames forming a montage covering the entire conduit length. Measured data analyzed in Excel.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A method for identifying a tumor product, comprising
   providing a tumor characterized by a vasculogenic program;
   sampling arterial influx to the tumor;
   sampling venous efflux from the tumor;
   measuring an amount of a composition in the influx;
   measuring an amount of the composition in the efflux; and
   identifying the composition as a tumor product when the amount of the composition in the efflux exceeds the amount of the composition in the influx.

2. The method of claim 1, wherein the tumor product is selected from the group consisting of cytokines, growth factors, morphogens, angiogenesis factors, and anti-angiogenesis factors.

3. The method of claim 1, wherein the tumor product is a cell.

4. A method for isolating a tumor product, comprising
   providing an implanted tumor characterized by a vasculogenic program;
   sampling venous efflux from the tumor, wherein the efflux comprises a tumor product; and
   isolating the tumor product from the efflux.

5. The method of claim 4, wherein the tumor product is selected from the group consisting of cytokines, growth factors, morphogens, angiogenesis factors, and anti-angiogenesis factors.

6. The method of claim 4, wherein the tumor product is a cell.

* * * * *